(12) United States Patent
Steinke et al.

(10) Patent No.: US 11,571,579 B2
(45) Date of Patent: Feb. 7, 2023

(54) SYSTEM AND METHOD FOR DETERMINATION OF CONNECTED NEUROSTIMULATION LEADS

(71) Applicant: Boston Scientific Neuromodulation Corporation, Valencia, CA (US)

(72) Inventors: G. Karl Steinke, Valencia, CA (US); Ara Sarian, Burbank, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 381 days.

(21) Appl. No.: 16/128,283

(22) Filed: Sep. 11, 2018

(65) Prior Publication Data

US 2019/0076659 A1 Mar. 14, 2019

Related U.S. Application Data

(60) Provisional application No. 62/557,640, filed on Sep. 12, 2017.

(51) Int. Cl.
*A61N 1/36* (2006.01)
*A61N 1/05* (2006.01)
(Continued)

(52) U.S. Cl.
CPC ......... *A61N 1/36185* (2013.01); *A61N 1/025* (2013.01); *A61N 1/05* (2013.01); *A61N 1/0551* (2013.01); *A61N 1/36* (2013.01); *A61N 1/36125* (2013.01); *A61N 1/37211* (2013.01); *A61N 1/0534* (2013.01); *A61N 1/362* (2013.01); *A61N 1/36062* (2017.08); *A61N 1/36067* (2013.01); *A61N 1/36082* (2013.01); *A61N 1/37241* (2013.01); *A61N 1/37247* (2013.01); *A61N 1/3956* (2013.01); *A61N 2001/083* (2013.01)

(58) Field of Classification Search
CPC ...... A61N 1/36185; A61N 1/025; A61N 1/05; A61N 1/0551; A61N 1/36; A61N 1/36125; A61N 1/37211; A61N 1/36062; A61N 1/0534; A61N 1/36067; A61N 1/36082; A61N 1/362; A61N 1/37241; A61N 1/37247; A61N 1/3956; A61N 2001/083
See application file for complete search history.

(56) References Cited

U.S. PATENT DOCUMENTS

| 4,964,407 A | 10/1990 | Baker, Jr. et al. |
| 6,181,969 B1 | 1/2001 | Gord |

(Continued)

OTHER PUBLICATIONS

International Search Report and Written Opinion regarding corresponding PCT Application No. PCT/US2018/050499, dated Dec. 19, 2018.

*Primary Examiner* — Christopher A Flory
(74) *Attorney, Agent, or Firm* — Lewis & Reese, PLLC

(57) ABSTRACT

The types of electrode leads that are connected to an implantable medical device are determined based on electrical parameters that are measured at the electrodes that are positioned on the leads. The different types of known electrode leads have different physical electrode arrangements that impact the measured electrical parameters. Properties in the measured electrical parameters that are indicative of the physical arrangements of electrodes of known types of electrode leads are utilized to determine the types of leads that are connected to the implantable medical device.

20 Claims, 14 Drawing Sheets

(51) Int. Cl.
  *A61N 1/02* (2006.01)
  *A61N 1/372* (2006.01)
  *A61N 1/362* (2006.01)
  *A61N 1/39* (2006.01)
  *A61N 1/08* (2006.01)

(56) References Cited

U.S. PATENT DOCUMENTS

| | | | |
|---|---|---|---|
| 7,831,307 B1* | 11/2010 | Moffitt | A61N 1/36071 607/46 |
| 8,463,402 B2 | 6/2013 | Zhu et al. | |
| 8,606,362 B2 | 12/2013 | He et al. | |
| 8,620,436 B2 | 12/2013 | Parramon et al. | |
| 8,731,679 B2 | 5/2014 | Ternes et al. | |
| 8,761,897 B2 | 6/2014 | Kaula et al. | |
| 8,768,453 B2 | 7/2014 | Parramon et al. | |
| 9,061,140 B2 | 6/2015 | Shi et al. | |
| 9,089,704 B2 | 7/2015 | Kelly | |
| 9,446,243 B2 | 9/2016 | Marnfeldt et al. | |
| 9,724,508 B2 | 8/2017 | Lamont et al. | |
| 2009/0198306 A1* | 8/2009 | Goetz | A61N 1/37264 600/407 |
| 2009/0234427 A1* | 9/2009 | Chinn | A61N 1/05 607/116 |
| 2010/0114210 A1* | 5/2010 | Donofrio | H01R 13/5224 607/37 |
| 2010/0137943 A1 | 6/2010 | Zhu | |
| 2011/0112609 A1 | 5/2011 | Peterson | |
| 2011/0270065 A1* | 11/2011 | Ternes | A61N 1/36114 607/32 |
| 2012/0016447 A1* | 1/2012 | Zhu | A61N 1/36185 607/62 |
| 2012/0116476 A1* | 5/2012 | Kothandaraman | G16H 40/40 607/45 |
| 2012/0123496 A1* | 5/2012 | Schotzko | A61N 1/3706 607/28 |
| 2012/0191153 A1 | 7/2012 | Swerdlow et al. | |
| 2012/0290034 A1 | 11/2012 | Rochat et al. | |
| 2013/0006333 A1* | 1/2013 | Kaula | A61N 1/08 365/189.011 |
| 2013/0184794 A1 | 7/2013 | Feldman et al. | |
| 2014/0067019 A1* | 3/2014 | Kothandaraman | A61N 1/37247 607/60 |
| 2015/0119958 A1 | 4/2015 | Li et al. | |
| 2016/0144194 A1* | 5/2016 | Roothans | A61N 1/37247 607/45 |
| 2017/0113049 A1 | 4/2017 | Kothandaraman | |

* cited by examiner

SYSTEM AND METHOD FOR DETERMINATION OF CONNECTED NEUROSTIMULATION LEADS

CROSS-REFERENCE TO RELATED APPLICATIONS

This is a non-provisional of U.S. Provisional Patent Application Ser. No. 62/557,640, filed Sep. 12, 2017, which is incorporated herein by reference, and to which priority is claimed.

FIELD OF THE TECHNOLOGY

The present disclosure relates to the identification of the types of leads that are connected to an implantable medical device (IMD) based on different physical electrode arrangements of the different types of leads.

INTRODUCTION

Neurostimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows focuses on a Deep Brain Stimulation (DBS) system, such as is disclosed in U.S. Patent Application Publication No. 2013/0184794, but the disclosed techniques are applicable to other neurostimulation devices as well.

As shown in FIG. 1, a DBS system typically includes an implantable pulse generator (IPG) 10 (more generally an implantable medical device), which includes a biocompatible device case 12 that is formed from a metallic material such as titanium. The case 12 typically comprises two components that are welded together, and it holds the circuitry and battery 14 (FIG. 2) necessary for the IPG 10 to function. The battery 14 may be either rechargeable or primary (non-rechargeable) in nature. The IPG 10 is coupled to electrodes 16 via one or more electrode leads 18 (four of which are shown). The proximal ends of the leads 18 include lead connectors 20 that are coupled to the IPG 10 at connector blocks 22 fixed in a header 24, which can comprise an epoxy for example. The lead connectors 20 are inserted into the connector blocks 22 through ports 8 in the header 24. Together, a port 8 and its associated connector block 22 form a device connector with which a lead connector 20 is associated. Contacts in the connector blocks 22 make electrical contact with corresponding contacts on the lead connectors 20, and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, each connector block 22 includes eight contacts and thus supports eight electrodes 16. Therefore, two four-electrode leads 18 include a single lead connector 20 that is inserted into a single connector block 22, one eight-electrode lead 18 includes a single lead connector 20 that is inserted into a single connector block 22, and one 16-electrode lead 18 includes two lead connectors 20 that are inserted into two connector blocks 22. Also shown in FIG. 1 is a lead adapter 19, which includes a female adapter connector 21 that is configured to receive a lead connector 20' that is not compatible with the IPG 10's connector block 22 and wire the lead 18's contacts to the compliant adapter connector 20. This can be useful, for example, for utilizing legacy leads 18 with a newer IPG 10 or for using a different manufacturer's leads 18 (e.g., previously-implanted leads 18 provided by a different manufacturer than the manufacturer of the IPG 10) with the IPG 10. While the illustrated system supports 32 electrodes 16 (i.e., eight electrodes for each of its four ports 8), the configuration of the connector blocks 22 and the number of supported electrodes 16 are application specific and can vary.

As shown in FIG. 2, IPG 10 contains a charging coil 30 for wireless charging of the IPG's battery 14 using an external charging device 50, assuming that battery 14 is a rechargeable battery. If IPG 10 has a primary battery 14, charging coil 30 in the IPG 10 and external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IPG 10, in plan and cross section views. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-held, portable housing.

External charger 50 provides power to recharge the IPG 10's battery 14 should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

In a DBS application, as is useful in the treatment of neurological disorders such as Parkinson's disease, the IPG 10 is typically implanted under the patient's clavicle (collarbone), and the leads 18 are tunneled through the neck and between the skull and the scalp where the electrodes 16 are implanted through holes drilled in the skull in the left and right sides of the patient's brain, as shown in FIG. 3. Specifically, the electrodes 16 may be implanted in the subthalamic nucleus (STN), the pedunculopontine nucleus (PPN), or the globus pallidus internus (GPi). Stimulation therapy provided by the IPG 10 has shown promise in reducing the symptoms of neurological disorders, including rigidity, bradykinesia, tremor, gait and turning impairment, postural instability, freezing, arm swing, balance impairment, and dystonia.

After the leads 18 and IPG 10 are implanted, the IPG 10 is configured. The configuration process is typically performed using a clinician's programmer system (CP System) 200 such as that illustrated in FIG. 4. CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 4, CP computer 202 is shown as a laptop computer that includes typical computer user interface means such as a screen 204, a mouse, a keyboard, speakers, a stylus, a printer, etc., not all of which are shown for convenience. CP computer 202 executes CP software 96, which software may be stored in the CP computer 202's non-volatile memory 220. One skilled in the art will recognize that execution of the CP software 96 in the CP computer 202 can be facilitated by control circuitry 222 such as a microprocessor, microcomputer, an FPGA, other digital logic structures, etc., which is capable of executing programs in a computing device. Execution of the CP software 96 causes the control circuitry 222 or other dedicated graphical processing circuitry to render a graphical user interface (GUI) 94.

Also shown in FIG. 4 is an accessory communication head 210 that is coupleable to a port of the CP computer 202, such as a USB port 206, to enable the CP computer 202 to communicate with the IPG 10 via a communication link 92 (e.g., to cause the IPG 10 to execute stimulation routines with different parameters in order to evaluate their effectiveness). Communication between the CP system 200 and the IPG 10 may comprise magnetic inductive or short-range RF telemetry schemes (as described above with respect to communications between the IPG 10 and the programmer 40), and in this regard the IPG 10 and the CP computer 202 and/or the communication head 210 (which can be placed proximate to the IPG 10) may include antennas compliant with the telemetry means chosen. For example, the communication head 210 can include a coil antenna 212a, a short-range RF antenna 212b, or both. The CP computer 202 may also communicate directly with the IPG 10, for example using an integral short-range RF antenna 212b, without the use of the communication head 210.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

An initial step in the IPG configuration process involves the specification of the type of electrode leads 18 that have been implanted (e.g., from a list of leads that are configured in the software 96) and the port 8 in which each lead connector 20 is positioned. While FIG. 1 generically illustrates electrodes 16 as aligned linearly along leads 18, such leads 18 commonly include different electrode arrangements. A particular IPG 10 may be compatible with a number of different types of leads 18, which can include, perhaps, leads 18 produced by a different manufacturer than the manufacturer of the IPG 10 through the use of adapters.

FIGS. 5A-5D illustrate examples of electrode leads 18 with different physical electrode arrangements. Lead 18A's eight electrodes 16 are all circumferential electrodes that are arranged linearly along the lead 18A. Lead 18B's eight electrodes 16 include circumferential electrodes at the proximal and distal ends (electrodes E1 and E8) of the electrode array and six segmented electrodes (electrodes E2-E7) between the circumferential electrodes. As used herein, segmented electrodes (or split-ring electrodes) are electrodes that extend around a portion of a lead 18B. Often multiple segmented electrodes are positioned at the same axial position along a lead 18. Lead 18B's segmented electrodes (electrodes E2-E7) are arranged with three electrodes at each of two axial positions, each segmented electrode spanning an approximately 110 degree arc around the lead 18B with approximately 10 degree spaces between neighboring segmented electrodes. Lead 18C's eight electrodes include three circumferential electrodes at its distal end (E1-E3), two circumferential electrodes at its proximal end (E7 and E8), and three segmented electrodes (E4-E6) between the two groups of circumferential electrodes. The space between the segmented electrodes E4-E6 and the circumferential electrode E7 is larger than the spacing between other adjacent electrode axial positions. Lead 18D is a paddle lead that includes eight surface electrodes that are arranged in a two-by-four array.

Although particular example leads 18 are illustrated in FIGS. 5A-5D, the type and placement of electrodes 16 along a lead is application-specific and therefore can vary. For example, a lead may include more or fewer segmented electrodes at a given axial position and more or fewer circumferential electrodes in addition to the segmented electrodes. As will be understood, because the segmented electrodes are separated by a non-conductive break, electrical stimulation that is directed to a segmented electrode propagates outward in the direction of the electrode rather than uniformly about the lead 18 as with circumferential electrodes. While the electrode leads 18 illustrated in FIGS. 5A-5D are referenced below to illustrate different patterns in the measurements acquired from their electrodes based on their different physical electrode arrangements, it will be understood that these examples are merely illustrative and that the techniques described below can be utilized to identify leads having different physical electrode arrangements from those depicted in FIGS. 5A-5D. Moreover, the example data sets below are ordered according to electrode number. For example, the first data point corresponds to electrode E1, the second data point corresponds to electrode E2, and so on.

In order to associate the implanted electrodes 16 with the current generation circuitry to which the electrodes 16 are connected, the CP GUI 94 may present a depiction such as that shown in FIG. 6, which shows the header 24 of the implanted IPG 10 with the ports 8 labeled as they are labeled on the actual IPG 10. Through the CP GUI 94, a user may then select the implanted leads 18 from a list of leads 18 that are configured in the CP software 96 and associate the lead connectors 20 with the port 8 in which they are positioned. In the illustrated example, the user has indicated that two leads 18A were implanted with their lead connectors 20A connected to ports "A" and "B" and that two leads 18B were implanted with their lead connectors 20B connected to ports "C" and "D". Given the known connection between the electrode nodes in the current generation circuitry (i.e., the node to which current designated for a particular contact in a particular connector block 22 is provided) and the contacts in the connector blocks 22 and the known connection between the contacts in the lead connectors 20 and electrodes 16 for the selected electrode leads 18, this designation establishes the connection between each electrode 16 and its corresponding electrode node in the current generation circuitry. With this association established, the connectivity between the current generation circuitry and the electrodes 16 is abstracted from the user and the stimulation therapy can be customized (e.g., via the CP software 96) by specifying the parameters of stimulation for the various electrodes 16 on the selected electrode leads 18. Such parameters can include pulse width, stimulation amplitude, frequency, and the electrode(s) 16 that serve as anodes and cathodes, for example. The IPG configuration process typically involves testing different stimulation parameters in order to identify the parameters that provide the most beneficial therapy for the patient.

DETAILED DESCRIPTION

Figure 7:
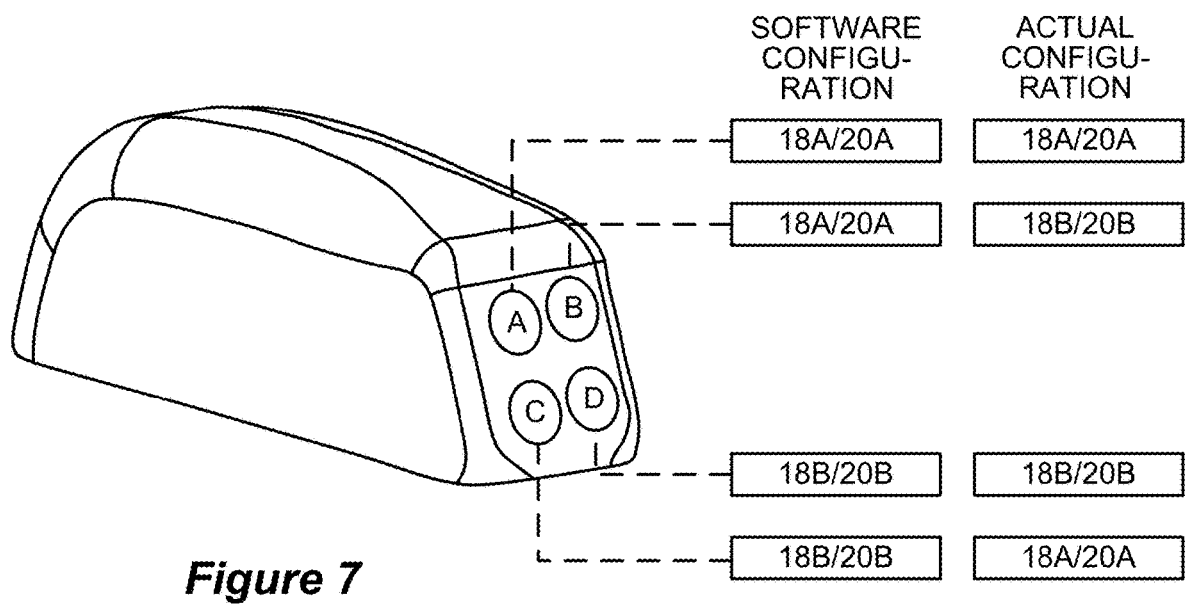
FIG. 7 shows an example of an incorrect assignment of lead connectors to IPG ports in accordance with an aspect of the disclosure.

The inventors have observed that the user association of lead connectors 20 with corresponding ports 8 of the implanted IPG 10 is subject to user error. For example, as illustrated in FIG. 7, the user's association established in the CP software 96 may not match the actual connections. In the example in FIG. 7, in the software configuration, the user has flipped the assignment of one of the leads 18A with one of the leads 18B. That is, one of the leads 18B is actually connected to port "B" of the IPG 10 and one of the leads 18A is actually connected to port "C" of the IPG 10. This type of error can have significant consequences. First, incorrect assignment in the CP software 96 can make it very difficult to configure the stimulation therapy. This is because stimulation that is being specified for a particular electrode is actually being delivered to a different electrode, and, therefore, a different anatomical location than what is intended. In addition, the software 96 relies upon the user assignments to configure other parameters in the IPG 10. For example, a segmented electrode may have a lower safe current limit than a circumferential electrode and therefore an incorrect assignment could enable a segmented electrode that is understood to be a circumferential electrode based on the incorrect assignment to be stimulated at a current that is higher than the specified safe current limit. Furthermore, the IPG 10 may be configured with various parameters that specify operation in a magnetic resonance imaging (MRI) environment. These MRI parameters often rely on the electrode type and can therefore be inaccurate based on an incorrect assignment.

Figure 8A:
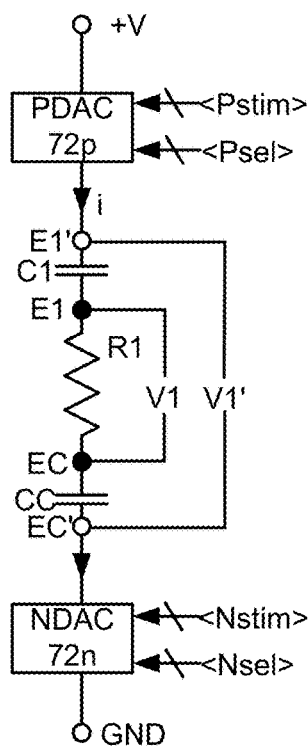
FIGS. 8A-8C show the configuration of an LPG's current generation circuitry in order to collect monopolar impedance data, bipolar impedance data, and induced field potential data to be used in determining which lead connectors are inserted into different ports of an IPG in accordance with an aspect of this disclosure.
Figure 8B:
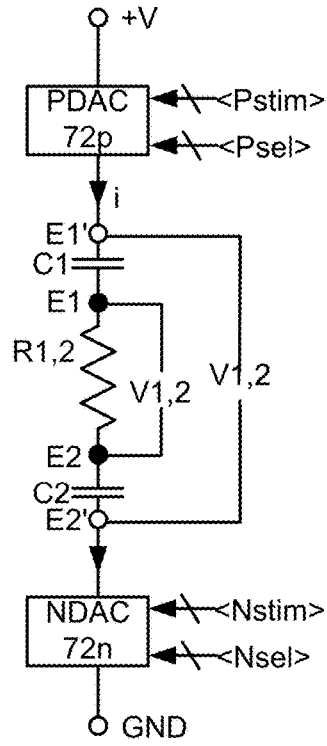
Figure 8C:
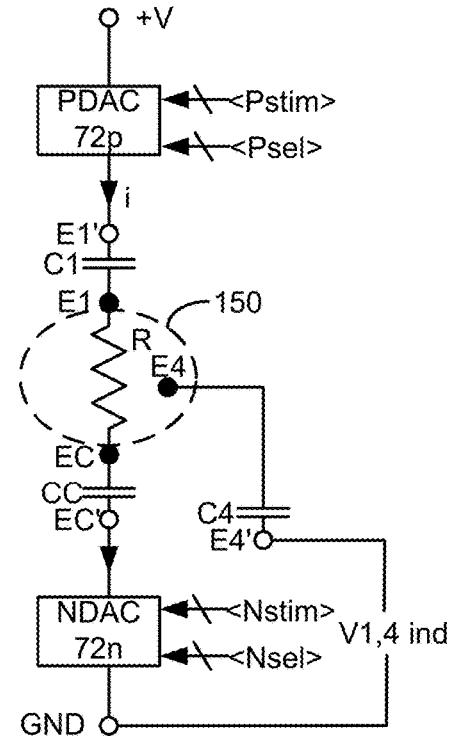

The present disclosure describes a system and technique to identify the types of leads 18 (or groups of electrodes) that are connected to an IPG 10's ports 8 to either verify a user's software port assignment or to eliminate the need for such user software assignments altogether. The disclosed system and technique rely upon the measurement and evaluation of impedance and induced field potential data from the connected electrodes. FIGS. 8A-8C show how the different impedance and induced field potential measurements used in the evaluation are collected.

The IPG 10's current generation circuitry includes one or more Digital-to-Analog Converters (DACs) 72 for receiving stimulation parameters and for forming the prescribed pulses at the selected electrodes. FIG. 8A shows a simple example of DAC circuitry 72 as used to provide a current pulse between selected electrode E1 and the IPG 10's case 12 (EC), which can be configured to act as an electrode, through a patient's tissue, R. DAC circuitry 72 as shown comprises two portions, denoted as PDAC 72$p$ and NDAC 72$n$. These portions of DAC circuitry 72 are so named due to the polarity of the transistors used to build them and the polarity of the current they provide. Thus, PDAC 72$p$ is formed from P-channel transistors and is used to source a current +I to the patient's tissue R via a selected electrode E1 operating as an anode. NDAC 72$n$ is formed of N-channel transistors and is used to sink current –I from the patient's tissue via a selected electrode EC (i.e., the IPG 10's case 12) operating as a cathode. It is important that current sourced to the tissue at any given time equal that sunk from the tissue to prevent charge from building in the tissue, although more than one anode electrode and more than one cathode electrode may be operable at a given time.

PDAC 72$p$ and NDAC 72$n$ receive digital control signals, denoted <Pstim> and <Nstim> respectively, to generate the prescribed pulses with the prescribed timing. In the example shown, PDAC 72$p$ and NDAC 72$n$ comprise current sources, and in particular include current-mirrored transistors for mirroring (amplifying) a reference current Iref to produce pulses with an amplitude (A). PDAC 72$p$ and NDAC 72$n$ could however also comprise constant voltage sources. Control signals <Pstim> and <Nstim> also prescribe the timing of the pulses, including their duration (D) and frequency (f). The PDAC 72$p$ and NDAC 72$n$ along with the intervening tissue R complete a circuit between a power supply +V and ground. The compliance voltage +V is adjustable to an optimal level to ensure that current pulses of a prescribed amplitude can be produced without unnecessarily wasting IPG power.

The DAC circuitry 72 (PDAC 72$p$ and NDAC 72$n$) may be dedicated at each of the electrodes, and thus may be activated only when its associated electrode is to be selected as an anode or cathode. See, e.g., U.S. Pat. No. 6,181,969. Alternatively, one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 72$p$ or NDAC 72$n$. See, e.g., U.S. Pat. No. 8,606,362. DAC circuitry 72 may also use a combination of these dedicated and distributed approaches. See, e.g., U.S. Pat. No. 8,620,436.

The current I is routed from the PDAC 72$p$ to electrode node E1' (a node in the IPG 10's current generation circuitry that is coupled to electrode E1 and is differentiated from electrode E1 by the prime designator). From electrode node E1', the current I flows through a blocking capacitor C1 to the electrode E1 and through the patient's tissue R to the IPG 10's case 12 (EC). The NDAC 72$n$ pulls the current I from the case EC through the blocking capacitor CC and to the electrode node EC'. Measurement circuitry in the IPG 10 is configured to measure the voltage between selected nodes. In FIG. 8A, the measurement circuitry is configured such that the voltage V1' between electrode nodes E1' and EC is measured. U.S. Pat. No. 9,061,140, which is incorporated herein by reference in its entirety, describes measurement circuitry and a corresponding measurement technique that can be utilized to remove the voltage across the blocking capacitors (C1 and CC) from the V1' measurement, thus providing the voltage V1 between electrodes E1 and EC. Using the measured voltage V1 and the known current I, the impedance R1 between electrodes E1 and EC can be calculated as R1=V1/I.

This initial type of monopolar impedance data (i.e., impedance between an electrode and the IPG 10's case 12) can be collected for each of the connected electrodes (using a common current amplitude for each), and it provides information about the types of electrodes that are connected to a particular port 8, and thus the type of lead(s) or portion thereof connected to the port 8.

Figure 9:
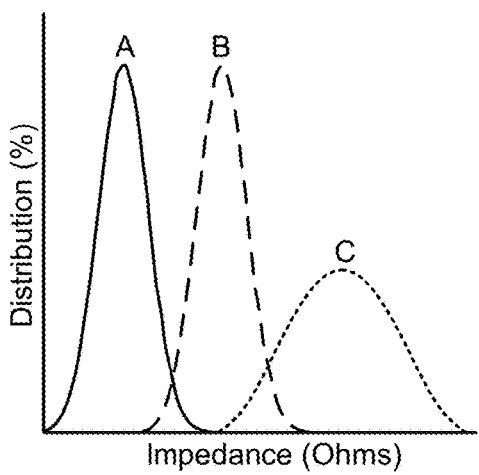
FIG. 9 shows an example distribution of monopolar impedance data for different types of electrodes in accordance with an aspect of this disclosure.

FIG. 9 illustrates example distributions of monopolar impedance measurements for example electrodes of different types (A, B, and C). The different types of electrodes can include circumferential electrodes of different dimensions, segmented electrodes of different dimensions, and/or paddle electrodes of different dimensions. The purpose of FIG. 9 is to illustrate that electrodes of different types have different monopolar impedance signatures that enable the different types of electrodes to be distinguished from each other.

Figure 1:
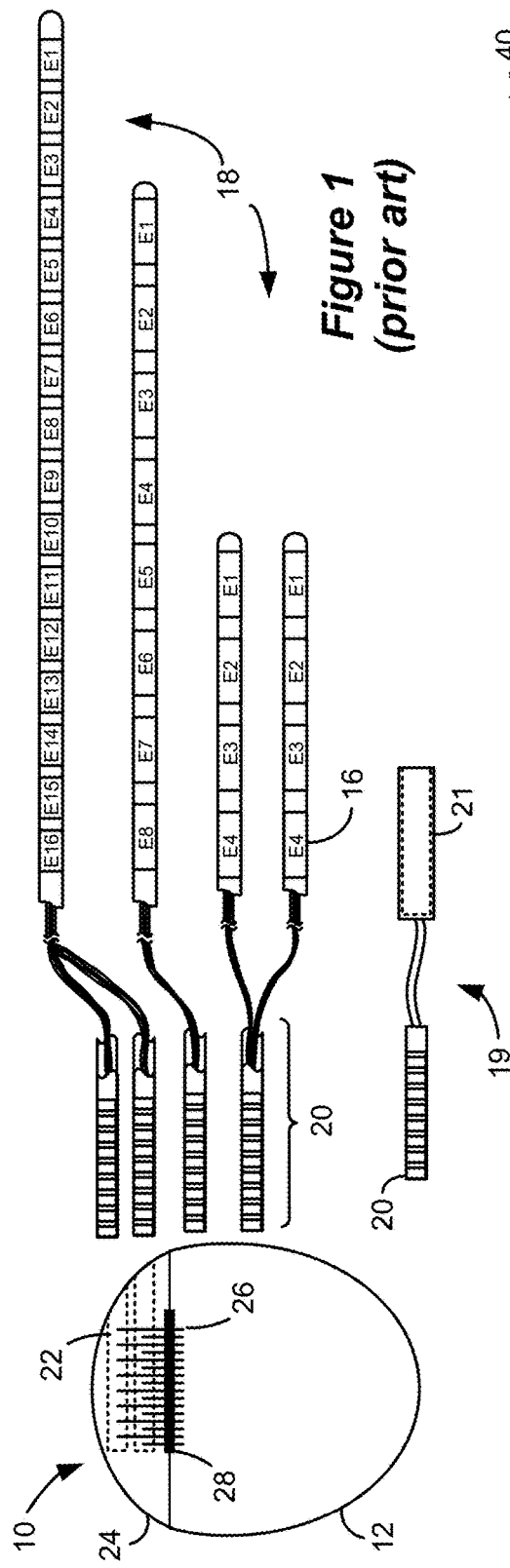
FIG. 1 shows an implantable pulse generator (IPG) with different electrode leads in accordance with the prior art.
Figure 2:
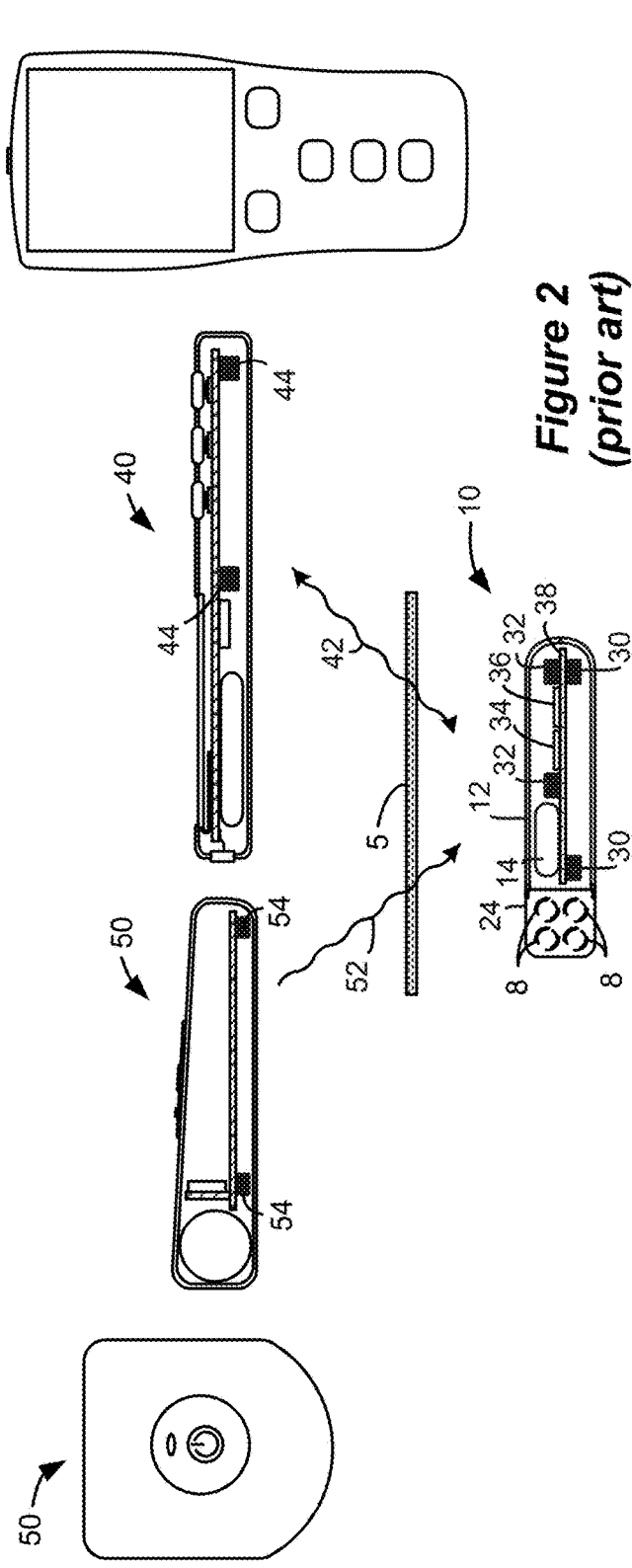
FIG. 2 shows a cross section of the IPG of FIG. 1 as implanted in a patient, as well as external devices that support the IPG, including an external charger and external controller in accordance with the prior art.
Figure 4:
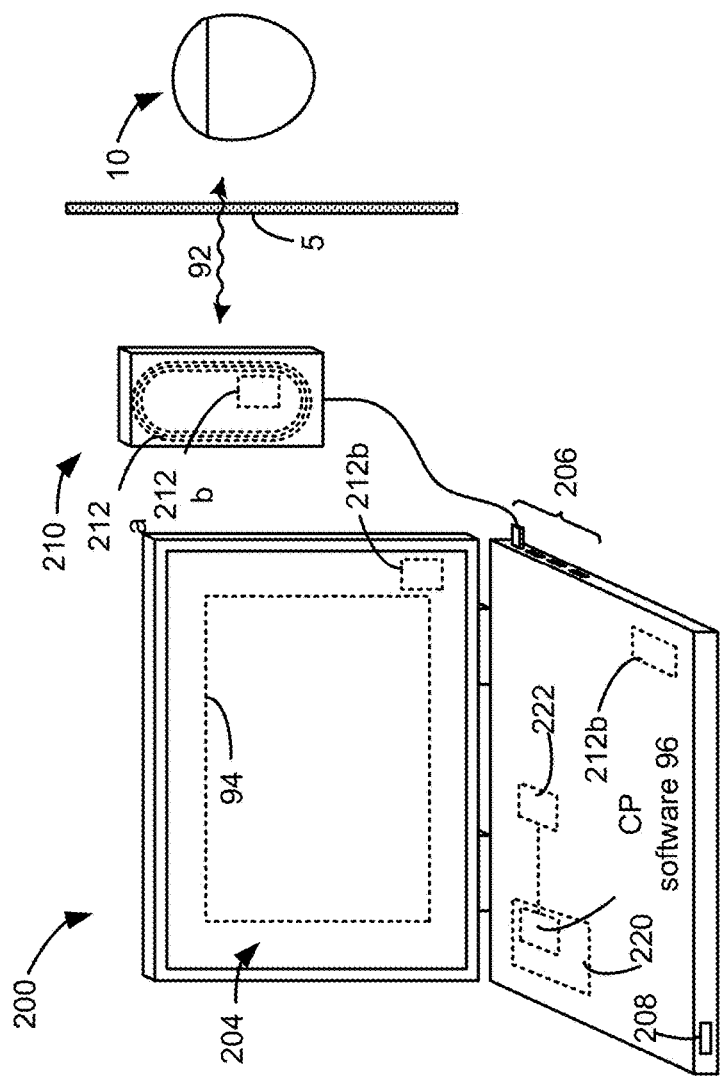
FIG. 4 shows components of a clinician's programmer system, including components for communicating with a neurostimulator in accordance with the prior art.
Figure 3:
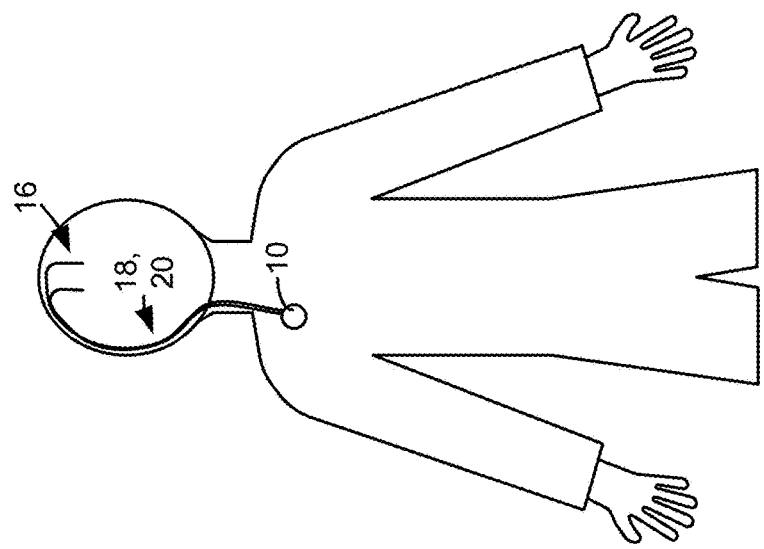
FIG. 3 shows implantation of the IPG in a patient in a Deep Brain Stimulation (DBS) application in accordance with the prior art.
Figure 5A:
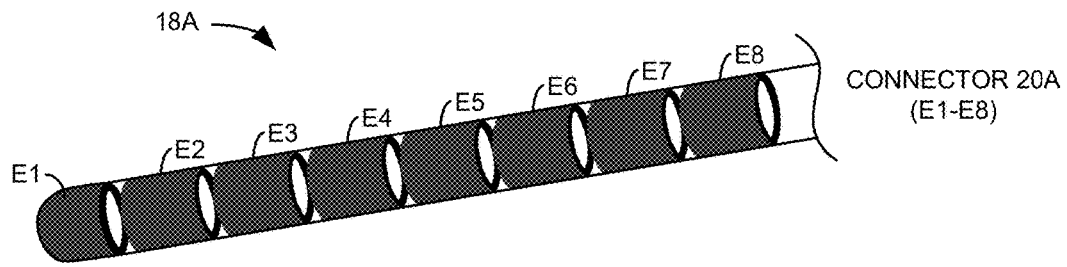
FIGS. 5A-5D show electrode leads with different physical electrode arrangements in accordance with an aspect of this disclosure.
Figure 5B:
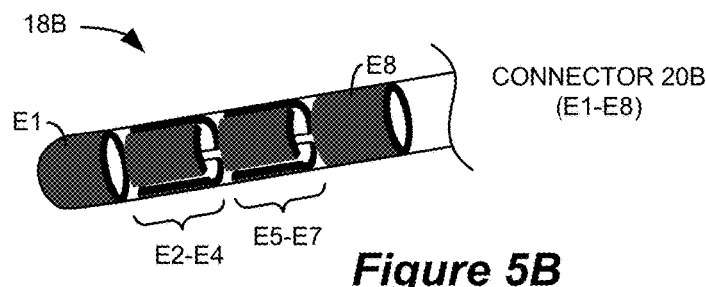
Figure 5C:
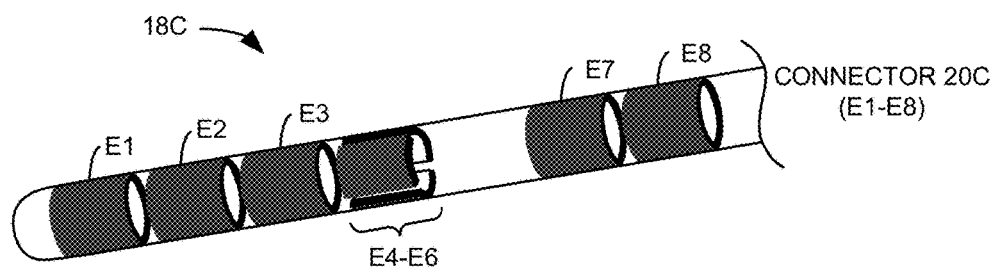
Figure 5D:
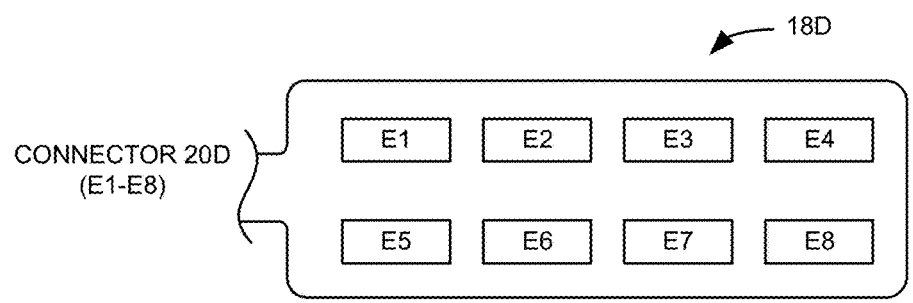
Figure 6:
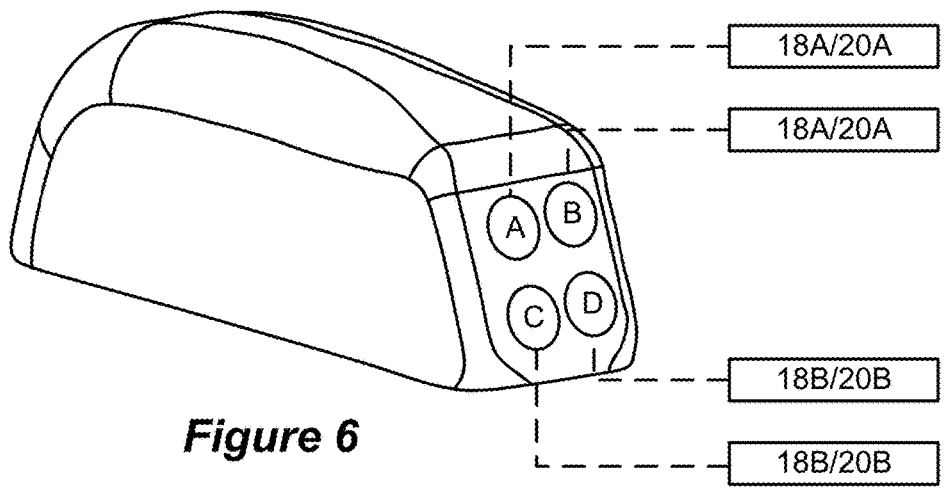
FIG. 6 shows an example graphical user interface that allows a user to assign lead connectors to the ports of the IPG in which they are inserted in accordance with an aspect of the disclosure.
Figure 10:
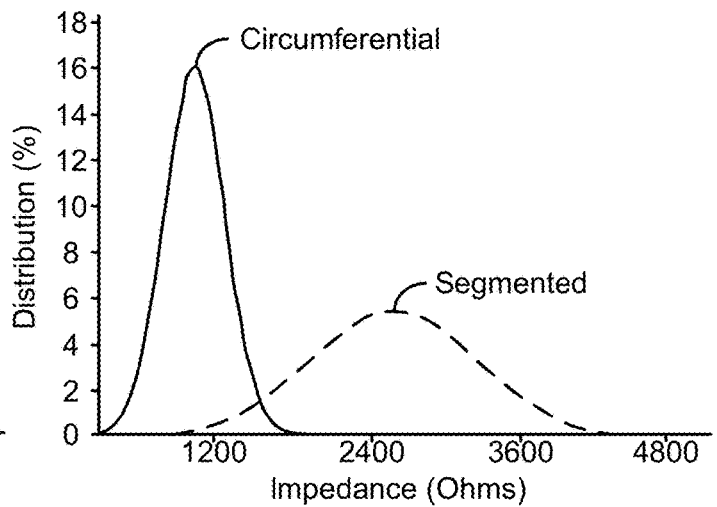
FIG. 10 shows an example distribution of monopolar impedance data for the circumferential and segmented electrodes for the electrode leads shown in FIGS. 5A-5C, in accordance with an aspect of this disclosure.

FIG. 10 offers a more concrete example of this using actual data for the circumferential and segmented electrodes for the leads shown in FIGS. 5A-5C. As illustrated, the circumferential electrodes generally display lower monopolar impedances than the segmented electrodes. This is due to the fact that circumferential electrodes result in the flow of current through a larger volume of tissue than segmented electrodes. While there is some variance in the data that results in an overlap in measured impedances between the different electrode types, the electrodes arranged on a single lead 18 (and thus positioned in the same tissue) often exhibit a pattern as a result of the distinction in monopolar impedances of circumferential and segmented electrodes. Accordingly, this feature (i.e., the physical arrangement of circumferential and segmented electrodes) results in a pattern in the monopolar impedance data that enables different lead types to be distinguished from one another.

Figure 11A:
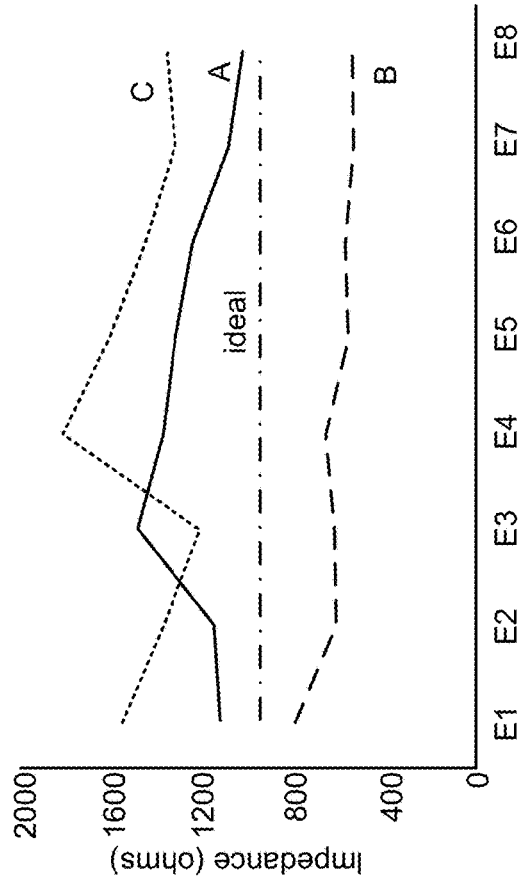
FIGS. 11A and 11B show example monopolar impedance data sets for the electrode leads shown in FIGS. 5A and 5B, respectively, in accordance with an aspect of this disclosure.
Figure 11B:
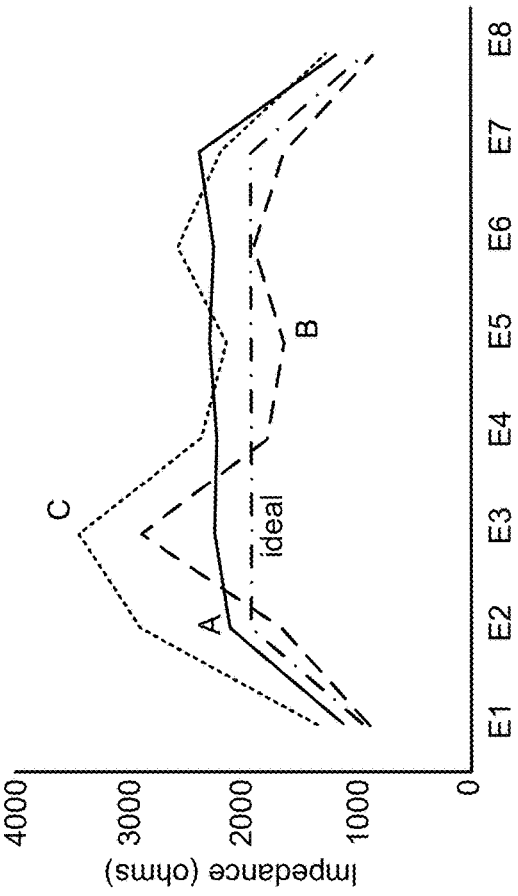
Figure 12:
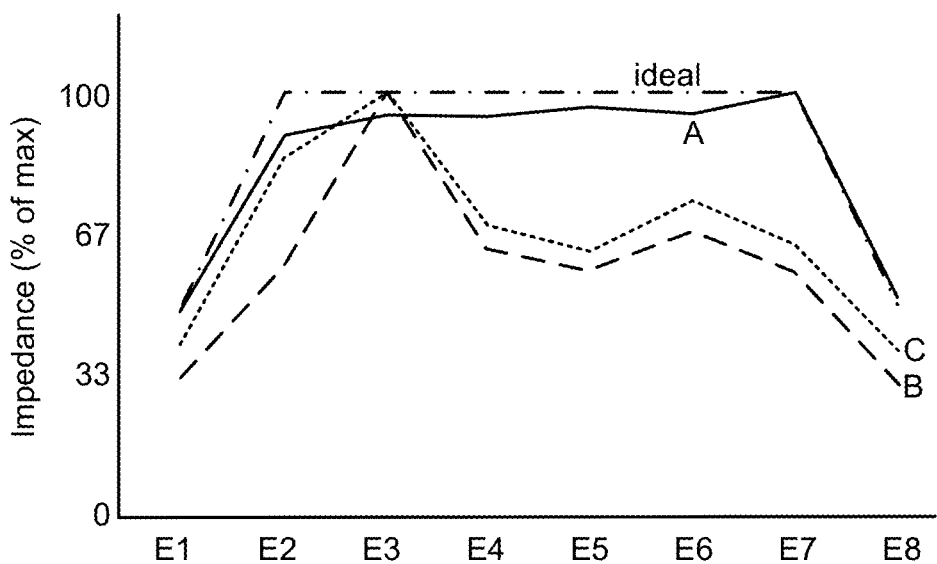
FIG. 12 shows example normalized monopolar impedance data for the data sets shown in FIG. 11B in accordance with an aspect of this disclosure.

FIGS. 11A and 11B illustrate three sample sets of measured monopolar impedance data along with an "ideal" data set for leads 18A and 18B, respectively. The different electrodes are plotted along the horizontal axis and their corresponding measured monopolar impedances are plotted along the vertical axis. As illustrated in FIG. 11A, because lead 18A includes eight circumferential electrodes, the measured impedance for each of the electrodes is approximately constant. While there is variation between the different data sets (e.g., data sets A and C exhibit higher impedances than data set B), the impedance measurements within any particular data set are relatively constant (i.e., they do not include a particular measurement that is substantially higher than other measurements as would be indicative of a segmented electrode). In FIG. 11B, on the other hand, in each of the data sets, the impedance measurements for electrodes E2-E7 are substantially higher (e.g., on the order of two times higher) than the impedance measurements for electrodes E1 and E8. This pattern corresponds to lead 18B's physical electrode arrangement (i.e., electrodes E1 and E8 are circumferential electrodes and electrodes E2-E7 are segmented electrodes). FIG. 12 shows the data sets in FIG. 11B (corresponding to lead 18B) as normalized. The normalized data sets are very well-aligned with the "ideal" data set. As can be seen from the example data sets in FIGS. 11A, 11B and 12, measured monopolar impedance values can be utilized to distinguish between different types of leads that are connected to an IPG.

FIG. 8B shows DAC circuitry 72 as configured to provide a current pulse between selected electrodes E1 and E2, through the patient's tissue, R. This arrangement is substantially similar to the arrangement shown in FIG. 8A except a lead-based electrode is selected to operate as the cathode rather than the IPG 10's case 12. The impedance measurement can be obtained in the same manner as described above by selecting the active anode and cathode electrode nodes in the measurement circuitry. In the specific example illustrated in FIG. 8B, the impedance R1,2 is measured between electrodes E1 and E2. Such bipolar impedance measurements can be collected for each pair of electrodes (using a common current amplitude for each). In one embodiment, the impedance between a pair of electrodes can be assumed to be equal regardless of the polarity of the electrodes (i.e., regardless of which electrode acts as the cathode and which acts as the anode), thus reducing the number of impedance measurements by one-half. Alternatively, the bipolar impedance measurements can be collected for both polarity arrangements for each electrode pair.

Figure 13:
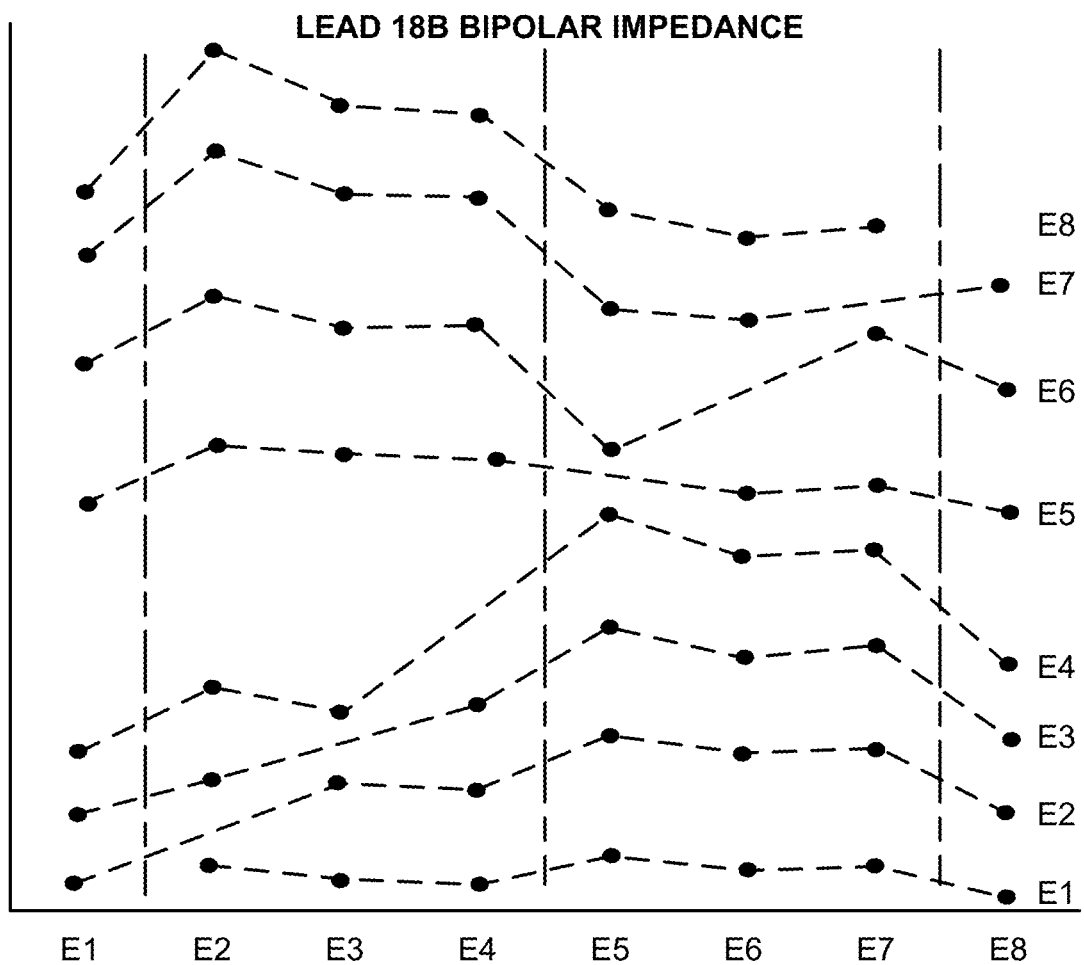
FIG. 13 shows an example bipolar impedance data set for the lead shown in FIG. 5B in accordance with an aspect of this disclosure.

FIG. 13 illustrates a full set of bipolar impedance measurements for lead 18B. In the graph in FIG. 13, each group of data points connected by a dashed line represents the impedance measurements collected in conjunction with a particular electrode. For example, the group of data points connected by the dashed line labeled E1 represents impedance measurements between electrode E1 and each of the other electrodes E2-E7. Each group includes seven data points that are representative of the impedance between the electrode associated with the data group and the other seven electrodes. In the data set shown, impedance measurements between a pair of electrodes are assumed to be equal regardless of electrode polarity. In order to better illustrate the relationships between the data points in each group, the groups have been separated vertically and therefore the vertical axis does not represent absolute impedance (only relative impedance within each particular group). The vertical lines separate electrodes at different axial positions along the lead 18B.

In general, the measured impedance in each of the groups is lower at electrodes E1 and E8. Just as with the monopolar impedance measurements described above, this provides an indication that electrodes E1 and E8 are circumferential electrodes while electrodes E2-E7 are segmented electrodes. In addition, the bipolar impedance data provides information about the location and grouping of electrodes. For example, in each of the groups, the electrode E2-E4 measurements are substantially similar and the electrode E5-E7 measurements are substantially similar, but the electrode E2-E4 measurements differ from the electrode E5-E7 measurements. This is due to the fact that the E2-E4 electrodes are identical segmented electrodes located at a first axial position on lead 18B and the E5-E7 electrodes are identical segmented electrodes located at a second axial position on the lead 18B. Notice also that the relationship between the electrode E2-E4 measurements and the electrode E5-E7 measurements changes based on the data group. In the electrode E1-E4 data groups, the electrode E2-E4 measurements are generally lower than the electrode E5-E7 measurements, but, in the electrode E5-E8 groups, the electrode E2-E4 measurements are generally higher than the electrode E5-E7 measurements. This relationship is due to the positioning of the electrodes along the lead 18B. The shorter distance through resistive tissue between any of electrodes E1-E4 and the segmented electrodes E2-E4 as compared to the distance between any of electrodes E1-E4 and the segmented electrodes E5-E7 results in lower impedance measurements. Similarly, the shorter distance through resistive tissue between any of electrodes E5-E8 and the segmented electrodes E5-E7 as compared to the distance between any of electrodes E5-E8 and the segmented electrodes E2-E4 results in lower impedance measurements. Thus, the bipolar impedance measurements provide additional information regarding the type of connected lead.

Figure 14:
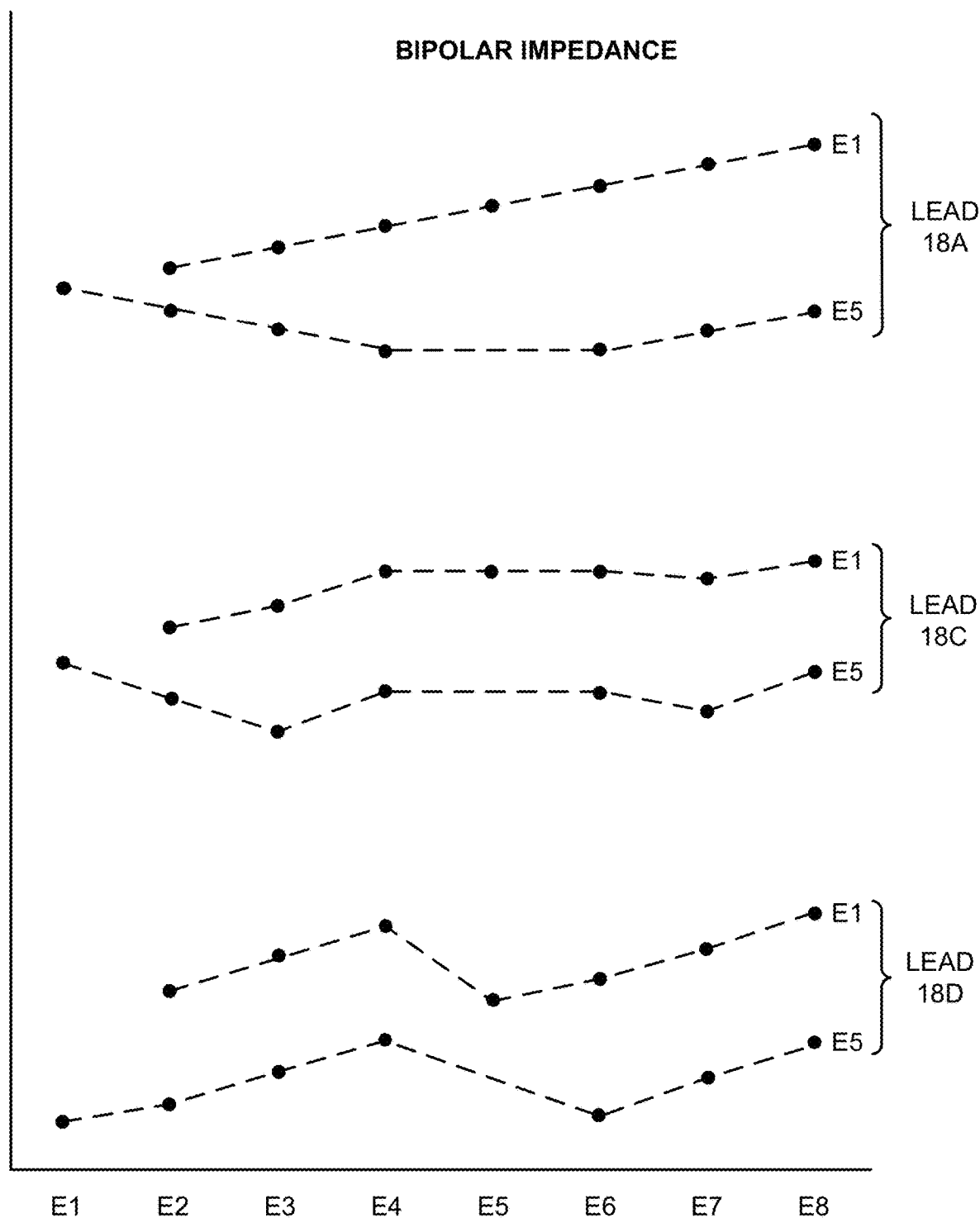
FIG. 14 shows partial idealized bipolar impedance data sets for various ones of the leads shown in FIGS. 5A-5D to illustrate differences in the bipolar impedance data in accordance with an aspect of this disclosure.

FIG. 14 shows an example of the usefulness of bipolar impedance data in differentiating between different types of leads 18. In particular, FIG. 14 illustrates idealized bipolar impedance measurements for common electrode groups for the other leads illustrated in FIGS. 5A-5D. Each of the electrode groups (i.e., the groups of data points connected by a dashed line) include bipolar impedance measurements between the electrode associated with the group and the other seven electrodes connected to the same lead connector. For each of the different leads, corresponding electrode groups for electrodes E1 and E5 are shown.

As illustrated, the bipolar impedance measurements for lead 18A increase linearly at each electrode away from the electrode associated with the group. For example, the impedance measurements for the electrode E1 group increase linearly from electrodes E2-E8. Similarly, the impedance measurements for the electrode E5 group increase linearly from electrodes E4-E1 and from electrodes E6-E8. This linear increase corresponds to the equal spacing of the circumferential electrodes along the lead 18A. The lead 18C, having different electrode spacing, exhibits different bipolar impedance data. The impedance measurements for the electrode E1 group increase at electrodes E2 and E3, which are circumferential electrodes at increasing distance from electrode E1, increase further and remain constant across electrodes E4-E6, which are segmented electrodes at a common axial location, and slightly decrease at electrode E7 before again increasing at electrode E8, which electrodes E7 and E8 are circumferential electrodes at increasing distance from electrode E1. The electrode E5 group exhibits the same impedance pattern related to electrode positioning. Note that in the E5 group, the impedance measured at electrodes E7 and E8 are higher than the impedance measured at electrodes E2 and E3 due to the increased spacing between electrode E5 and electrodes E7 and E8 as compared to the distance between electrode E5 and electrodes E2 and E3.

The bipolar impedance data for lead 18D displays a unique pattern as a result of its arrangement of leads in a two-by-four array. The bipolar impedance between any pair of electrodes positioned on the paddle lead 18F is a function of the distance between the electrodes. Because the electrodes are equally-spaced in rows of four with electrodes E1 through E4 in a first row and electrodes E5 through E8 in a second row, the bipolar impedance measurements are approximately linear across the electrodes in a particular row.

While the data depicted in FIG. 14 is idealized and is only shown for two of the eight electrodes associated with each lead, the full set of bipolar impedance data for a set of eight electrodes includes clearly identifiable trends that enable the differentiation of different types of leads. This bipolar impedance data can enable differentiations between electrode leads that are difficult or impossible using monopolar impedance data alone.

FIG. 8C shows DAC circuitry 72 as configured to provide a current pulse between electrode E1 and the IPG 10's case 12 (EC) in the same manner as described above with respect to FIG. 8A. However, in FIG. 8C, the measurement circuitry is configured to measure the voltage at an electrode (electrode E4 in the configuration illustrated in FIG. 8C) other than those that are used for stimulation. During a stimulation pulse (between E1 and EC in the configuration illustrated in FIG. 8C), an electric field 150 is generated in the patient's tissue, R. The field 150 is strongest nearest to the stimulating electrode, and its strength decreases with increasing distance from the stimulating electrode. As a result, the measurement of a voltage between a non-stimulating electrode (e.g., E4) and a reference voltage (e.g., a ground reference) provides an indication of the distance between the stimulating electrode and the electrode at which the measurement was taken. In FIG. 8C, the voltage at electrode E4 couples through the capacitor C4, and the induced voltage measurement V1,4 and is measured between the electrode node E4' and a ground reference node. Induced voltage measurements can be obtained for each different pair of electrodes (i.e., between electrode E1 and each of the other electrodes when stimulation is between electrode E1 and the case 12, between electrode E2 and each of the other electrodes when stimulation is between electrode E2 and the case 12, and so on). While it is not strictly necessary, in a preferred embodiment, the IPG 10's case 12 is selected as one of the stimulating electrodes and the selected amplitude of stimulation is held constant for the collection of all of the induced field potential measurements. Selection of the case 12 as one of the stimulating electrodes provides a cleaner induced field potential data set as its distance from the leads 18 avoids any interference that may otherwise be present were two lead-based electrodes used as stimulating electrodes. The induced field potential measurements can be obtained at any point during the stimulation pulse.

In one embodiment, the induced voltage measurements can be assumed to be the same for a pair of electrodes regardless of which electrode was used as the stimulating electrode and which was used as the measuring electrode. For example, the voltage induced at electrode E2 when electrode E1 operates as the stimulating electrode can be assumed to be the same as the voltage induced at electrode E1 when electrode E2 operates as the stimulating electrode. Alternatively, two separate measurements can be taken for each pair of electrodes with each electrode in the pair operating as the stimulating electrode in one measurement and the measuring electrode in the other measurement.

Figure 15:
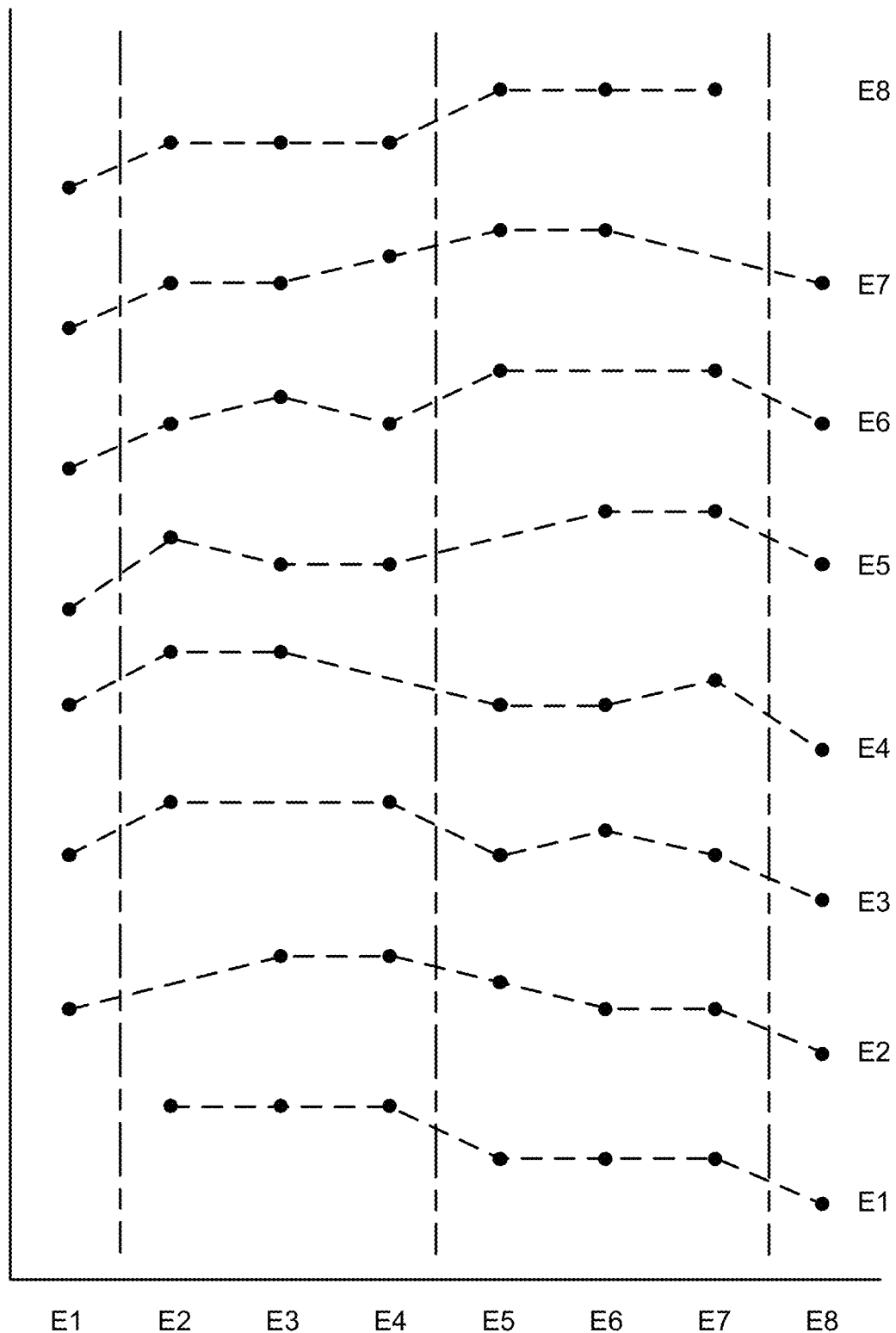
FIG. 15 shows idealized induced field potential data for the lead shown in FIG. 5B in accordance with an aspect of this disclosure.

FIG. 15 illustrates a full set of idealized induced field potential measurements for lead 18B. In the graph in FIG. 15, each group of data points connected by a dashed line represents the field potentials induced by stimulation of a single electrode. For example, the group of data points connected by the dashed line labeled E1 represents the field potential that is induced at each of the other electrodes E2-E7 when electrode E1 operates as the stimulating electrode. Each group includes seven data points that are representative of the field potential that is induced at the other seven electrodes. In the data set shown, induced field potential is assumed to be equal regardless of which electrode is the stimulating electrode (e.g., the induced potential at electrode E2 as a result of stimulation using electrode E1 is assumed to be equal to the induced potential at electrode E1 as a result of stimulation using electrode E2), but, again, this is not strictly necessary. In order to better illustrate the relationships between the data points in each group, the groups have been separated vertically and therefore the vertical axis does not represent absolute potential (only relative potential within each particular group).

The induced field potential data is similar to the bipolar impedance data in that it provides information regarding the relative positioning of electrodes along the lead. It differs from bipolar impedance data, however, in that it is not affected by electrode type (e.g., circumferential or segmented). Thus, the induced field potential data provides a purer indication of relative electrode positioning. This is indicated in the data set that is plotted in FIG. 15. As illustrated in FIG. 5B, electrodes E1 and E8 are circumferential electrodes that are separated by two groups of segmented electrodes (E2-E4 and E5-E7) at different axial locations. The vertical lines in FIG. 15 separate electrodes that are positioned at different axial locations along the lead 18B. The induced field potential data provide clear indications about the grouping of electrodes on the lead 18B as well as the electrodes' position. As illustrated, within each data group, the induced field potential is similar for segmented electrodes at a common axial position but different from the induced field potential for segmented electrodes at a different axial position. Moreover, the magnitude of the induced field potential for the segmented electrodes at a common axial position differs as a function of the distance between the stimulating and measuring electrodes. For example, the induced field potential at electrodes E2-E4 is higher than the induced field potential at electrodes E5-E7 for data groups E1-E4, but the opposite is true for data groups E5-E8. This illustrates that, as would be expected, the induced field potential is greater when the measuring electrode is closer to the stimulating electrode. The induced field potential at each of the circumferential electrodes E1 and E8 is a function of the electrode's distance from the stimulating electrode.

In addition to providing information regarding the grouping of segmented electrodes, the induced field potential data also illustrates an azimuthal linking between segmented electrodes at a same azimuthal position about the lead 18B. For example, in the electrode E2 group, the induced field is higher at electrode E5 than at electrodes E6 and E7, which are positioned at the same axial location as electrode E5. The higher field that is induced is a result of the common azimuthal position of electrodes E2 and E5 and the corresponding reduced distance between those electrodes. This same relationship can be seen in each of the data groups between pairs of azimuthally aligned electrodes E2 and E5, E3 and E6, and E4 and E7. As can be seen from FIG. 15, induced field potential data provides further information that can be used to differentiate between different types of leads 18.

Figure 16:
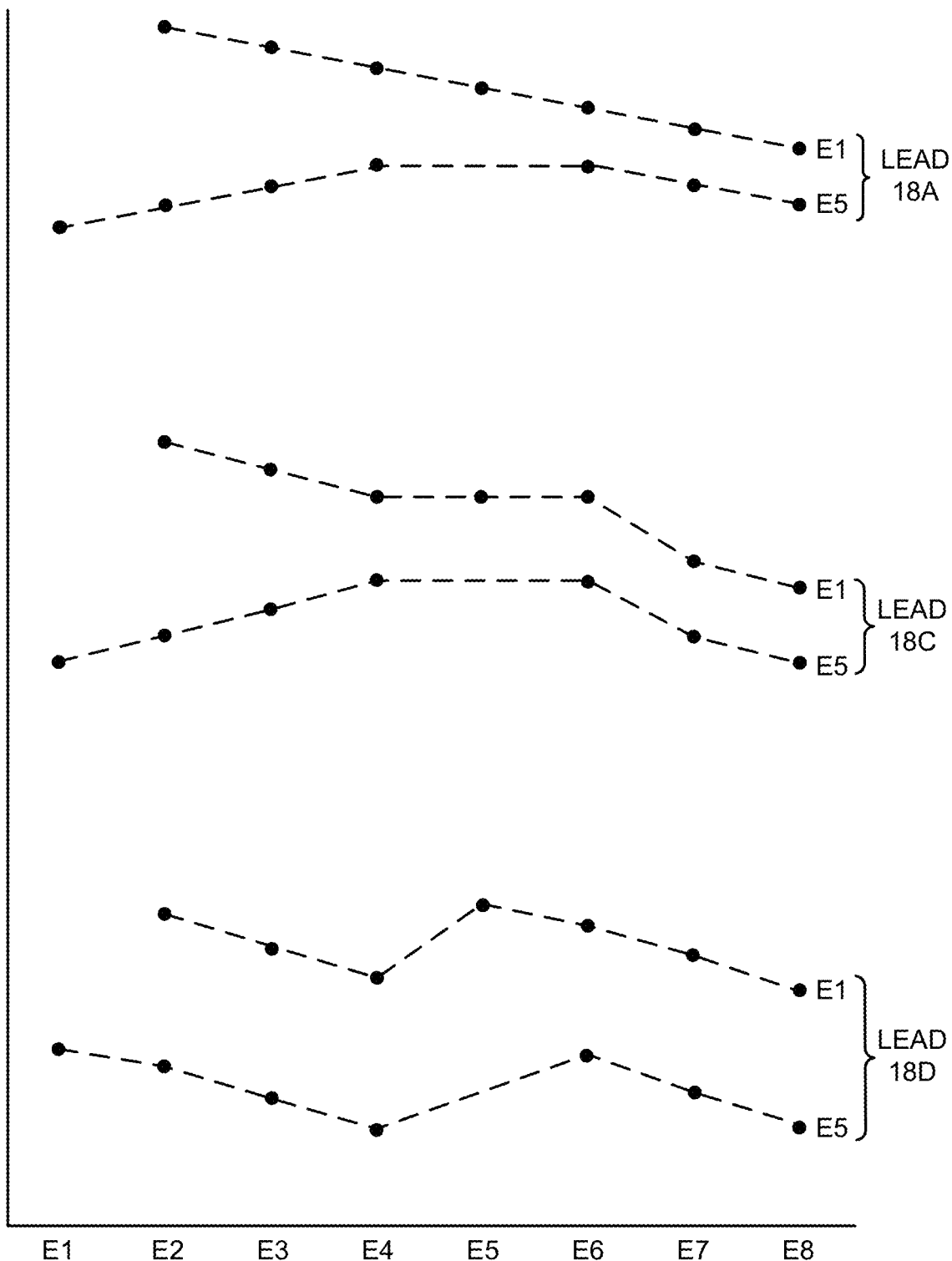
FIG. 16 shows partial idealized induced field potential data sets for various ones of the leads shown in FIGS. 5A-5D to illustrate differences in the induced field potential data in accordance with an aspect of this disclosure.

FIG. 16 illustrates idealized induced field potential measurements for common electrode groups for the other leads illustrated in FIGS. 5A-5D. Each of the electrode groups (i.e., the groups of data points connected by a dashed line) include induced field potential measurements between the electrode associated with the group and the other seven electrodes connected to the same lead. Moreover, for each of the different leads, corresponding electrode groups for electrodes E1 and E5 are shown.

As illustrated, the induced field potential data for lead 18A decreases linearly with increasing distance from the stimulating electrode. This is again related to the even spacing between the circumferential electrodes along lead 18A. The induced field potential data for lead 18C shows the positioning of electrodes E1, E2, E3, E4-E6, E7, and E8 at different axial locations along the lead 18C. In addition, the induced field potential data for lead 18C illustrates the large spacing between electrodes E4-E6 and electrode E7 as a larger difference in induced potential between the electrodes at these positions than between other adjacent axial positions. The induced field potential data for lead 18D shows a linear decrease with increasing distance from the stimulating electrode. While the data depicted in FIG. 16 is idealized and is only shown for two of the eight electrodes associated with each lead 18, the full set of induced field potential data for a set of eight electrodes includes clearly identifiable trends based on different physical electrode arrangements that enable the differentiation of different types of leads.

Figure 17:
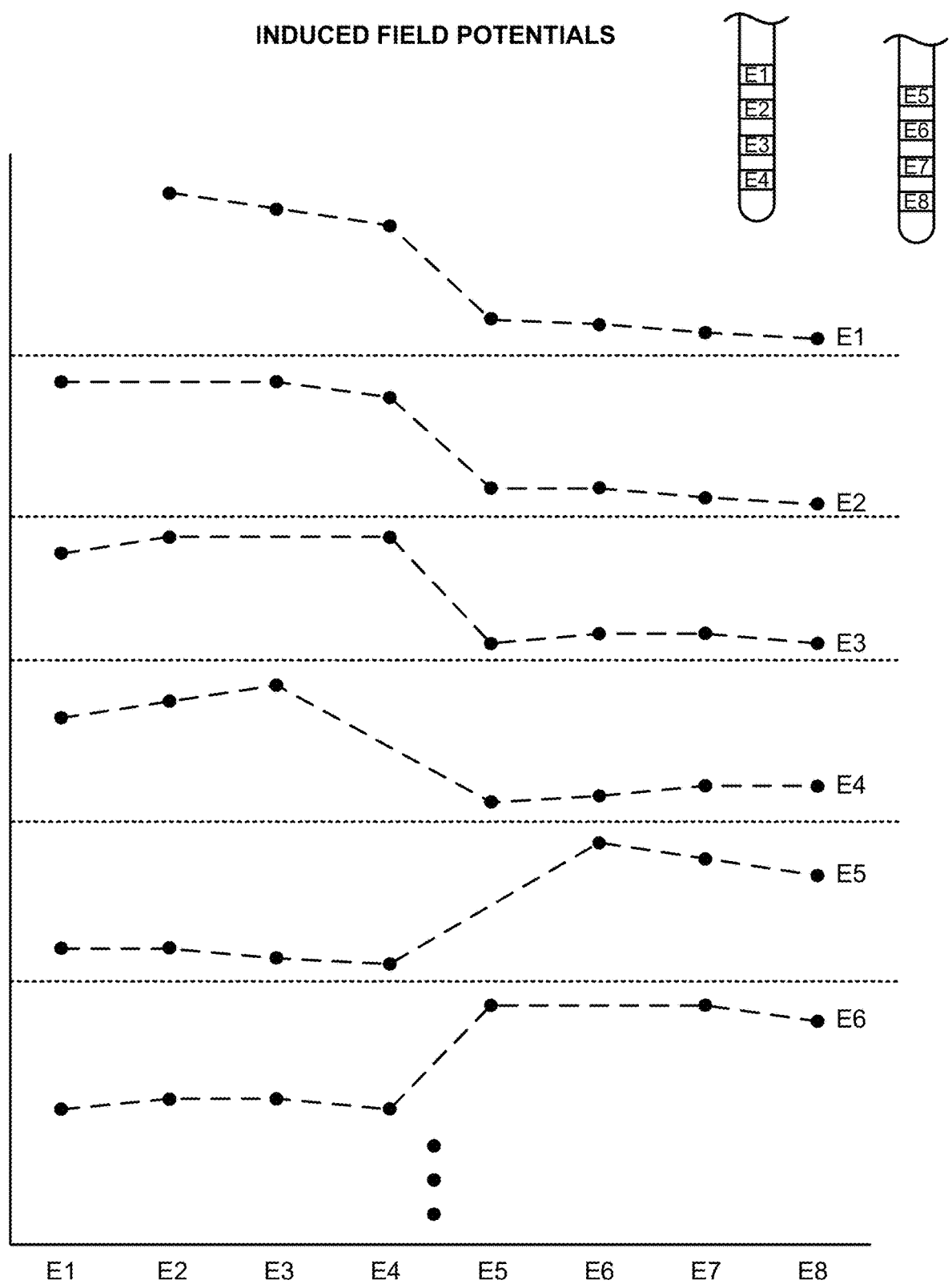
FIG. 17 shows idealized induced field potential data sets for electrodes on different example leads in accordance with an aspect of this disclosure.

FIG. 17 illustrates the use of induced field potential data to distinguish between electrodes that are associated with different leads. This can be particularly useful, for example, for identifying the type of electrode leads when there is not a 1:1 correspondence between a lead 18 and a lead connector 20 (e.g., two four-electrode leads sharing a single lead connector, one 16-electrode lead having two separate lead connectors, etc.). FIG. 17 illustrates idealized induced field potential data for the two four-electrode leads shown at the top of the figure. As can be seen in the data, the groups of electrodes on the different leads are clearly distinguishable. When any electrode on a lead is stimulated, the induced field potential is much higher at the other electrodes that are positioned on the same lead as the stimulating electrode and much lower at each of the electrodes on the other lead.

As the above example monopolar impedance, bipolar impedance, and induced field potential data indicates, different groups of electrodes can be distinguished from each other based on data that is indicative of their different physical electrode arrangements. Such different physical electrode arrangements may include different types of electrodes (e.g., segmented and circumferential electrodes of different dimensions), different axial positions and groupings of electrodes, different azimuthal alignment of electrodes on a lead, and different electrode spacings along a lead.

Figures 18, 19:
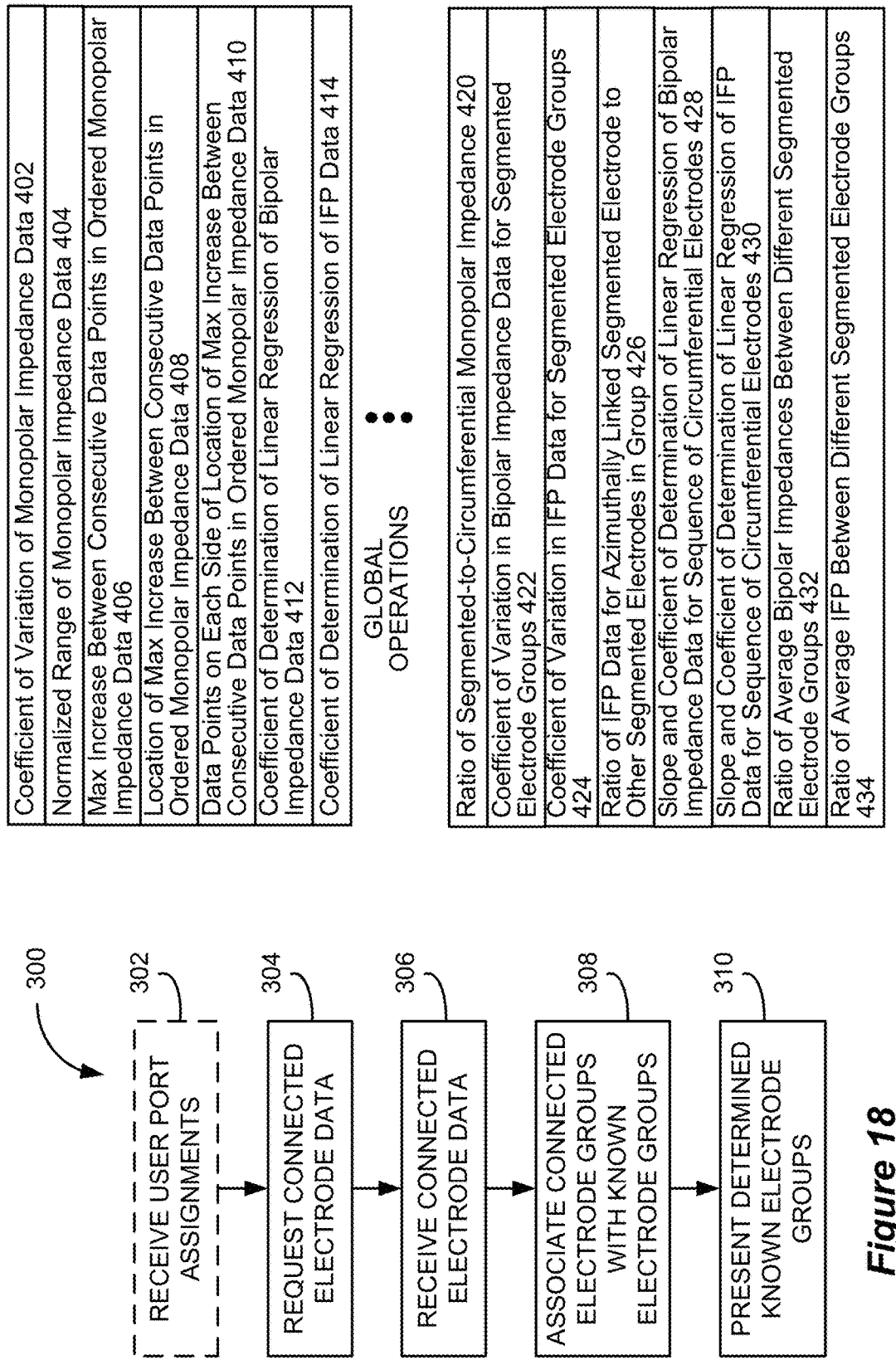
FIG. 18 shows a flowchart indicating the steps in a process to determine the types of lead connectors that are connected to the different ports of an IPG in accordance with an aspect of this disclosure.
FIG. 19 shows different types of operations that can be performed on data measured from the electrodes connected to an IPG's ports in order to determine the types of leads (and their associated lead connectors) that are connected to the different ports in accordance with an aspect of this disclosure.

FIG. 18 illustrates a process 300 that utilizes properties in a data set that are indicative of a physical arrangement of electrodes in a known electrode group to associate a group of electrodes that is connected to an IPG 10 with the known electrode group. The term electrode group is used here to describe electrodes that are associated with each other such as being connected to a common lead connector 20, positioned on a common lead 18, etc. While process 300 could be performed at any time, it is typically executed after implantation of an IPG 10 and as part of the above-described IPG configuration process. In a preferred embodiment, process 300 is executed on an external device such as CP computer 202 and is therefore incorporated into CP software 96. In another embodiment, process 300 may be executed on a different external device such as controller 40. For purposes of this description, process 300 is described in terms of its execution on CP computer 202.

Process 300 begins with the optional receipt of user port assignments (step 302). Such port assignments can be received in the manner described above through user selection of the leads 18 (or lead connectors 20) that are inserted in each port 8 of the IPG 10 via the software 96, for example. After receiving the user port assignments, or, alternatively, if no user port assignments are received, connected electrode data is requested from the IPG 10 (step 304). The connected electrode data can include all or a subset of the monopolar impedance, bipolar impedance, and induced field potential data described above. In one embodiment, a first subset of the data may be initially requested and additional data may be subsequently requested if needed. For example, the initial data request may include a request for monopolar impedance data and intra-port bipolar impedance and induced field potential data (i.e., bipolar impedance and induced field potential data between electrodes connected to the same port 8 but not across different ports 8). Similarly, the initial data request may include a request for monopolar impedance data only. In one embodiment, the amount and type of data requested may be based upon the user port assignment. For example, if the user port assignment specifies leads 18 that can likely be verified with a subset of data, only the required subset of data may be requested. Likewise, if the user port assignment specifies leads 18 that will necessarily require a larger set of data for verification, the larger set of data may be requested. In any event, the data request is communicated to the IPG 10, such as via the communication link 92.

In response to the data request, the requested data is received (step 306). The requested data may comprise data that is routinely collected by the IPG 10 and may therefore be readily available. Alternatively, all or some portion of the data may be collected by the IPG 10 only upon request, in which case the process 300 may wait while the data is collected by the IPG 10. Once received, the connected electrode data is processed (step 308) to associate connected electrode groups with known electrode groups. More specifically, the connected electrode data is evaluated using a classifier to associate connected groups of electrodes with one of the known electrode groups (i.e., the lead groups that are programmed into the software) based on properties in the data that are indicative of different physical arrangements of electrodes in known electrode groups.

In one embodiment, the connected electrode data is initially evaluated on a port-by-port basis, so the classifier is configured to discriminate between different groups of electrodes connected to different lead connectors 20 (and thus different ports 8) as opposed to the electrodes on a full lead (e.g., a 16-electrode lead). In one embodiment, a classifier is manually configured to identify patterns or characteristics in the connected electrode data that are indicative of different known electrode groups.

FIG. 19 illustrates several examples of the operations that might be performed to identify patterns in the data that are associated with different physical arrangements of electrodes for the different known electrode groups (e.g., the group of electrodes on a single lead 18 or the group of electrodes connected to a single lead connector 20). The operations may be performed on the raw data from the IPG 10, or the data may be pre-processed to normalize the data, remove anomalies, etc. In one embodiment, such anomalies may be indicative of improper connection of a lead connector 20 with a device port 8. For example, the impedance data may be very high for one of the terminal contacts associated with a port 8 but normal for the other contacts. Such a situation is indicative of a failure to fully seat the lead connector 20 in the connector block 22, which results in the incorrect alignment of contacts in the lead connector 20 and connector block 22 (i.e., contact 2 in the lead connector block is coupled to contact 1 in the lead connector 20, and so on). This type of situation may therefore be presented to the user as a warning of the incorrect insertion. In one embodiment, the user may be prompted to correct the issue before attempting to initiate the process 300 again. In an alternative embodiment, the process 300 may shift the data to accommodate the incorrect insertion (i.e., shift the contact 2 data to contact 1, etc.) in order to attempt to identify or verify the type of known electrode group that is improperly connected. After manipulation of the data to account for any anomalies, etc. the various operations illustrated in FIG. 19, as well as other related operations, may be performed.

The global operations do not rely upon the known properties of the different types of leads 18. That is, the global operations are applied to the data associated with a group of electrodes as a whole and not to subsets of such data based on different electrode arrangements of the known electrode groups. The coefficient of variation of monopolar impedance 402 represents the variance in the monopolar impedance data set, which variance is higher for electrode groups that include different electrode types (i.e., both circumferential and segmented). By way of example, for the monopolar impedance data illustrated in FIGS. 11A and 11B, the coefficient of variation for electrode groups associated with a single electrode type (i.e., lead 18A) is generally less than 15% whereas the coefficient of variation for electrode groups associated with different electrode types (i.e., lead 18B) is generally greater than 20%. Similarly, the normalized range of monopolar impedance data 404 (i.e., the ratio of the range of the data to the mean), like operation 402, provides an indication of variability in the monopolar impedance data set, which is much higher for electrode groups having different types of electrodes. For the monopolar impedance data illustrated in FIGS. 11A and 11B, the normalized range for electrode groups associated with a single electrode type is generally less than about 50% whereas the normalized range for leads associated with different electrode types is generally greater than about 80%. Thus, the operations 402 and 404 can provide a beneficial first indication of the type of electrode groups that are connected to an IMD.

The max increase between any pair of consecutive data points in an ordered set of monopolar impedance data 406 associated with a particular electrode group, like the variance metrics described above, provides an indication about whether the electrode group includes connections to electrodes of different types. A higher max increase indicates a higher likelihood that the electrode group includes connections to electrodes of different types. The location of the max increase 408 (i.e., the position in the data set at which the max increase occurs such as between the second and third data points in the ordered set) indicates the number of circumferential electrodes and the number of segmented electrodes in the electrode group. The specific data points 410 that are on each side of the max increase 408 provide an indication of the electrode numbers of the segmented electrodes and the circumferential electrodes in the electrode group. The table below shows the monopolar impedance data for lead 18B that is identified as data set "A" in FIG. 11B.

| Data Point | 1 | 2 | 3 | 4 | 5 | 6 | 7 | 8 |
|---|---|---|---|---|---|---|---|---|
| Impedance (ohms) | 1137 | 2124 | 2259 | 2246 | 2299 | 2263 | 2385 | 1206 |

The ordered data set is shown in the table below along with the point-to-point increases between consecutive data points.

| Data Point | 1 | 8 | 2 | 4 | 3 | 6 | 5 | 7 |
|---|---|---|---|---|---|---|---|---|
| Impedance (ohms) | 1137 | 1206 | 2124 | 2246 | 2259 | 2263 | 2299 | 2385 |
| Point-to-point Increase | | 69 | 918 | 122 | 13 | 4 | 36 | 86 |

As indicated in the ordered data set, the largest point-to-point increase occurs between the second and third points in the ordered set, and data points one and eight (which correspond to electrodes E1 and E8) are below the max increase. This correctly indicates that electrodes E1 and E8 are circumferential electrodes and electrodes E2-E7 are segmented electrodes.

The coefficient of determination (i.e., $R^2$) of the linear regression of bipolar impedance data 412 and induced field potential data 414 provide an indication of the linearity of the increase/decrease of the impedance and field potential with increasing/decreasing electrode number. A linear regression may be performed, for example, on the bipolar impedance and/or induced field potential data for a terminal electrode data group (i.e., the first or eighth electrode data group) for the lead connector being evaluated, and the coefficient of determination may be calculated to determine how well the linear regression fits the data. Because the bipolar impedance and induced field potential data for segmented electrodes at a common axial position are substantially equal, the data is less linear than corresponding data for circumferential electrodes. Thus, a higher coefficient of determination of a linear regression of either bipolar impedance or induced field potential data is generally indicative of the presence of a larger number of circumferential electrodes as opposed to segmented electrodes.

Unlike the global operations, the lead-specific operations take advantage of the known properties of the known electrode groups to manipulate the connected electrode data in different ways. The ratio of segmented-to-circumferential monopolar impedance 420, for example, may be calculated for a given monopolar impedance data set using the known electrode arrangements associated with the different lead connectors. For example, the ratio 420 may be calculated using the average monopolar impedance at data points two through seven (corresponding to segmented electrodes E2-E7) and the average monopolar impedance at data points one and eight (corresponding to circumferential electrodes E1 and E8) to determine if the monopolar impedance data set matches lead 18B. When the correct electrode grouping is utilized, the ratio 420 typically approaches a value of 2:1.

The coefficient of variation in bipolar impedance 422 and induced field potential 424 data can be evaluated across different electrode subgroupings within a group of electrodes to identify groups of segmented electrodes that are located at a common axial position. The coefficient of variation is relatively small in both the bipolar impedance and induced field potential data sets for segmented electrodes that are positioned at the same axial location, and the values can therefore help distinguish between different electrode groups. For example, the coefficient of variation across data points two through four and data points five through seven would typically be lower for lead 18B than for lead 18C, because the data points are associated with axially-grouped segmented electrodes in the former but span across different axial groups in the latter. Conversely, the coefficient of variation across data points four through six would typically be lower for lead 18C than lead 18B for the same reason.

The ratio of the induced field potential at azimuthally-linked electrodes to other segmented electrodes positioned at the same axial position 426 also provides an indication of segmented electrode grouping, and, thus, the type of electrode group. The ratio 426 can be computed for different electrode arrangements of known electrode groups, and the ratio is typically higher when the correct arrangement is used. By way of example, for lead 18B, the following pairs of electrodes are azimuthally linked: E2 and E5, E3 and E6, and E4 and E7. In the induced field potential data group for any one of these electrodes, its pair electrode will typically have a higher induced field potential than the other segmented electrodes at the same axial position. For example, as indicated in FIG. 15, in the electrode E2 group, electrode E5 has a higher induced field potential than electrodes E6 and E7, in the electrode E3 group, electrode E6 has a higher induced field potential than electrodes E5 and E7, and so on. As a result, the ratio of the induced field potential of azimuthally-linked segmented electrodes to other segmented electrodes at the same axial position is higher when the correct grouping is identified.

The slope and coefficient of determination of a linear regression of bipolar impedance data 428 and induced field potential data 430 across a series of data points can provide an indication about whether the data points correspond to a sequence of evenly-spaced circumferential electrodes at different axial positions (as opposed to segmented electrodes at the same axial position). These values can therefore be calculated for data points corresponding to known sequences of circumferential electrodes such as data points one through eight of lead 18A. When the slope and coefficient of determination, which can be calculated for different electrode groups, indicate a linear relationship across the selected data points, there is a higher likelihood that the electrodes corresponding to those data points are circumferential electrodes. Therefore, the values 428 and 430 can be used to distinguish between different leads 18.

The ratio of average bipolar impedance data 432 and induced field potential data 434 across different sets of data points, and the point at which the ratio flips, provides an indication of segmented electrode grouping. For example, as illustrated in FIG. 15, the ratio of the average induced field potential for data points two through four (corresponding to electrodes E2-E4) to the average induced field potential for data points five through seven (corresponding to electrodes E5-E7) in the electrode E1-E4 data groups is greater than unity. However, the same ratio for the electrode E5-E8 data groups is less than unity. The ratio flips starting at the fifth data group because the fifth data group corresponds to an electrode (E5) at a new axial position. These ratios therefore provide an additional indicator of segmented electrode grouping.

It will be understood that the listed operations are merely illustrative and not exhaustive. Based on the disclosed relationships, one of ordinary skill in the art will be capable of identifying further operations for classifying connected electrode data for electrode groups having different electrode arrangements. Moreover, it will be understood that the operations may be arranged in a manner that efficiently arrives at a determination of a known electrode group such as a decision tree. While the operations have been described in terms of their performance on data sets corresponding to a single lead 18 or lead connector 20, the classifier may include operations that are performed across data sets for different lead connectors 20 (e.g., bipolar impedance and/or induced field potential measurements between electrodes associated with different lead connectors 20). In one embodiment, intra-connector data may be evaluated initially and inter-connector measurements may be subsequently evaluated to confirm and/or further classify connected leads.

In addition to the described data classification operations, the classifier may also be programmed with various logical rules. For example, the classifier may be programmed such that both lead connectors of a multi-connector lead must be identified together (i.e., there can't be one connector of a multi-connector lead without the other connector).

While different manual classification operations have been described, classification may also be performed using a classifier that is trained using machine learning techniques. In this context, machine learning involves supplying a program a (preferably large) number of connected electrode data sets and their associated known electrode group (i.e., the known lead connector 20 or lead 18 that is associated with the data set). The program recognizes patterns in the data in the supplied data sets and, based on the patterns, generates a model that can be used to identify the electrode group that results in a future set. The data sets that are provided to the machine learning program may include the user port assignments, which may be considered by the program.

Regardless of the configuration of the classifier, its output is the determined known group of electrodes that is associated with each of the IMD 10's ports 8, which is presented to the user (310). The classifier may additionally be configured to determine and present one or more confidence measures. A first confidence measure may be described as a match confidence measure. A match confidence measure may represent the level of agreement between the data associated with a connected group of electrodes and the corresponding data for its determined known electrode group. Such a match confidence measure may be calculated using known statistical techniques for the comparison of the degree of similarity between two sets of data. A second confidence measure may be described as an evaluation confidence measure. The evaluation confidence measure may represent the degree of confidence in the determination of the matching known electrode group. The evaluation confidence measure may differ from the match confidence measure, for example, when a determination of a known electrode group is made on the basis of a more limited amount of data. For example, the limited amount of data may agree strongly with corresponding data for the determined known electrode group thus resulting in a high match confidence, but, because the amount of data is limited, the evaluation confidence may still be lower. The use of limited data may occur, for example, when statistical anomalies that are believed to be associated with open or short circuits are removed from a sample data set or when the analysis is performed on a more limited set of data (e.g., based on monopolar impedance alone, based on intra-port bipolar and/or induced field potential data, etc.). The evaluation confidence measure may be determined based on the amount of data that is utilized in associating the connected electrode group with a known electrode group as compared to the total amount of data that could be utilized. In making this determination, the different types of data may be weighted differently based on their usefulness in distinguishing between different groups of electrodes.

Figure 20:
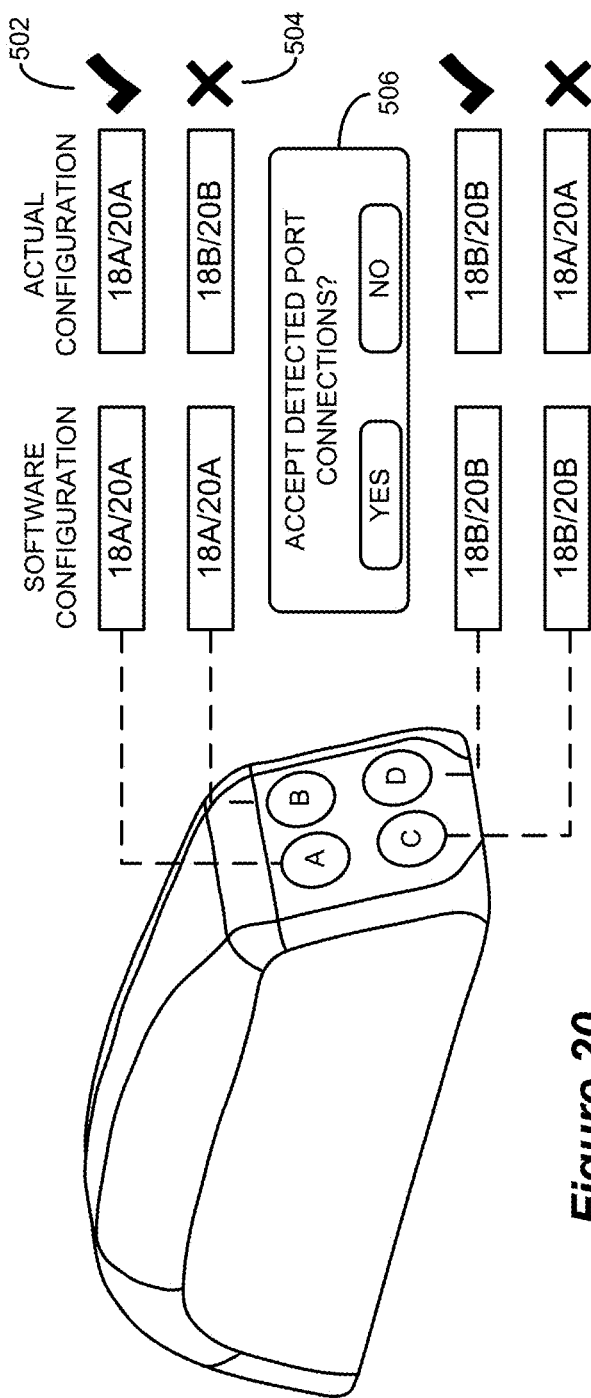
FIG. 20 shows an example graphical user interface that displays the determined types of leads (and their associated lead connectors) that are connected to an IPG's ports in conjunction with a user's assignment of types of leads (and their associated lead connectors) to the ports in accordance with an aspect of this disclosure.

FIG. 20 shows an example improved GUI 94' that may be used to present the determined electrode groups that are associated with each port of the IPG 10. As indicated in the GUI 94', when the port assignment matches that supplied by the user, a verification 502 of the user's assignment (e.g., a check mark or some other symbol of verification) is presented via the GUI 94'. When the port assignment disagrees with that supplied by the user, a mismatch indicator 504 (e.g., an "X" or some other symbol of the mismatch) is presented to the user via the GUI 94'. Regardless of whether the determined port assignment matches the user assignment or whether the user even made an assignment, the user may be presented with an interface 506 to confirm and accept the determined port assignments via the GUI 94'. As can be seen, the process 300 provides a mechanism for associating a group of electrodes that are connected to an IPG 10 with a known electrode group (e.g., a group of electrodes connected to a particular lead connector 20) based on properties in data from the connected group of electrodes that is indicative of a physical electrode arrangement in the associated known electrode group.

Figure 21:
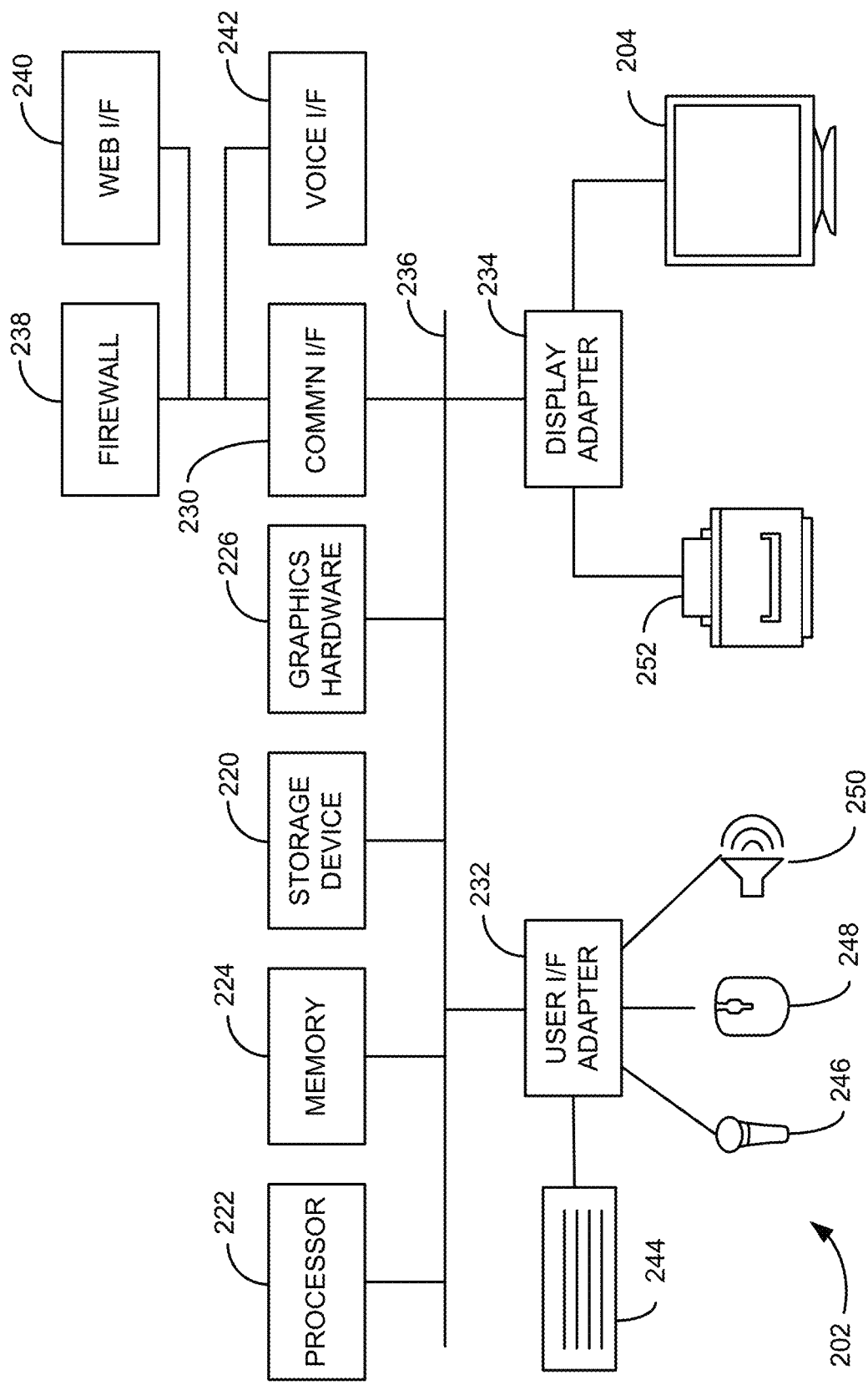
FIG. 21 illustrates a representative computing environment on which software that provides a process for determining the types of leads (and their associated lead connectors) that are connected to an IPG's ports may be executed in accordance with an aspect of the disclosure.

FIG. 21 illustrates the various components of an example CP computer 202 that may be configured to execute CP software 96 that incorporates the process 300. The CP computer 202 can include the processor 222, memory 224, storage 220, graphics hardware 226, communication interface 230, user interface adapter 232 and display adapter 234—all of which may be coupled via system bus or backplane 236. Memory 224 may include one or more different types of media (typically solid-state) used by the processor 222 and graphics hardware 228. For example, memory 224 may include memory cache, read-only memory (ROM), and/or random access memory (RAM). Storage 220 may store media, computer program instructions or software (e.g., CP software 96), preference information, device profile information, and any other suitable data. Storage 220 may include one or more non-transitory computer-readable storage mediums including, for example, magnetic disks (fixed, floppy, and removable) and tape, optical media such as CD-ROMs and digital video disks (DVDs), and semi-conductor memory devices such as Electrically Programmable Read-Only Memory (EPROM), Electrically Erasable Programmable Read-Only Memory (EEPROM), and USB or thumb drive. Memory 224 and storage 220 may be used to tangibly retain computer program instructions or code organized into one or more modules and written in any desired computer programming language. Communication interface 230 (which may comprise, for example, the ports 206 or 208) may be used to connect the CP computer 202 to a network. Communications directed to the CP computer 202 may be passed through a protective firewall 238. Such communications may be interpreted via web interface 240 or voice communications interface 242. Illustrative networks include, but are not limited to: a local network such as a USB network; a business' local area network; or a wide area network such as the Internet. User interface adapter 232 may be used to connect a keyboard 244, microphone 246, pointer device 248, speaker 250 and other user interface devices such as a touch-pad and/or a touch screen (not shown). Display adapter 234 may be used to connect display 204 and printer 252.

Processor 222 may include any programmable control device. Processor 222 may also be implemented as a custom designed circuit that may be embodied in hardware devices such as application specific integrated circuits (ASICs) and field programmable gate arrays (FPGAs). The CP computer 202 may have resident thereon any desired operating system.

While the CP system 200 has been described and illustrated as communicating directly with the IPG 10, the CP system 200 may additionally or alternatively be configured to communicate with different types of neurostimulators. For example, the CP system 200 may interface with an external trial stimulator that mimics the operation of the IPG 10 but that is positioned outside of the body to evaluate therapies during a trial phase. As will be understood, the CP software 96 may be stored on a medium such as a CD or a USB drive, pre-loaded on a computing device such as the CP computer 202, or made available for download from a program repository via a network connection. Moreover, while process 300 has been described as being performed on an external device, certain portions of the process 300 may instead be performed by the IPG 10 itself. For example, the IPG may measure the connected electrode data and the IPG's control circuitry may be configured to process such connected electrode data itself to associate connected groups of electrodes with known electrode groups. In such an embodiment, the IPG 10 may be configured to transmit its results to an external device so that the determined known electrode groups might be displayed to a user.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. A system, comprising:
a neurostimulator comprising a plurality of device connectors, wherein each device connector is configured to receive one of a plurality of leads having a plurality of electrodes;
an external device configured to communicate with the neurostimulator; and
a non-transitory computer-readable medium in the external device having instructions stored thereon to cause control circuitry in the external device to:
receive via an interface of the external device a user assignment of one of a plurality of lead types to at least one of the device connectors, wherein the lead types are distinguishable based on the physical arrangement of their electrodes;

obtain data from a lead connected to at least one of the device connectors, wherein the data from each lead comprises measurements taken from a group of electrodes in the lead indicative of a physical arrangement of the plurality of the electrodes on the lead;

evaluate the data to associate one of the lead types with each of the at least one device connectors to which a lead is connected; and determine for each device connector whether the user assignment of the lead type to that device connector matches the lead type associated with that device connector based on the evaluated data.

2. The system of claim 1, wherein each of the plurality of leads comprises a lead connector and is received by the neurostimulator through connection of the lead connector with one of the device connectors.

3. The system of claim 1, wherein the computer-readable medium further comprises instructions to cause the control circuitry to present on the interface an indication of the lead type that is associated with each of the at least one device connectors.

4. The system of claim 3, wherein the computer-readable medium further comprises instructions to cause the control circuitry to present on the interface an indication of the user assignment of the one of the plurality of lead types to the at least one of the device connectors.

5. The system of claim 1, wherein the data obtained from each lead comprises measurements of impedance between each of the electrodes in the group of electrodes and a case of a neurostimulator.

6. The system of claim 1, wherein the data obtained from each lead comprises measurements of impedance between one or more pairs of the electrodes in the group of electrodes.

7. The system of claim 1, wherein the data obtained from each lead comprises measurements of an electric potential that is induced at one or more of the electrodes in the group of electrodes when a current is sourced or sunk from a different one or more of the electrodes.

8. The system of claim 1, wherein one of the lead types comprises a physical electrode arrangement in which a first group of segmented electrodes are positioned at a common axial position.

9. The system of claim 1, wherein one of the lead types comprises a physical electrode arrangement in which a first electrode in a first group of segmented electrodes at a first axial position is azimuthally aligned with a second electrode in a second group of segmented electrodes at a second axial position.

10. The system of claim 1, wherein one of the lead types comprises a physical electrode arrangement comprising one or more circumferential electrodes and one or more segmented electrodes.

11. The system of claim 1, wherein one of the lead types comprises a physical electrode arrangement in which a sequence of circumferential electrodes are evenly spaced at different axial positions.

12. The system of claim 1, wherein the computer-readable medium further comprises instructions to cause the control circuitry to determine for each device connector a match or evaluation confidence between the user assignment of the lead type to that device connector and the lead type associated with that device connector based on the evaluated data.

13. The system of claim 1, wherein the instructions to evaluate the data comprise a classifier.

14. A method usable in conjunction with a neurostimulator comprising a plurality of device connectors, wherein each device connector is configured to receive one of a plurality of leads having a plurality of electrodes, the method comprising;

receiving at an interface of an external device a user assignment of one of a plurality of lead types to at least one of the device connectors, wherein the lead types are distinguishable based on the physical arrangement of their electrodes;

obtaining at the external device data from a lead connected to at least one of the device connectors, wherein the data from each lead comprises measurements taken from a group of electrodes in the lead indicative of a physical arrangement of the plurality of the electrodes on the lead;

evaluating the data at the external device to associate one of the lead types with each of the at least one device connectors to which a lead is connected; and determining at the external device for each device connector whether the user assignment of the lead type to that device connector matches the lead type associated with that device connector based on the evaluated data.

15. The method of claim 14, wherein each of the plurality of leads comprises a lead connector and is received by the neurostimulator through connection of the lead connector with one of the device connectors.

16. The method of claim 14, further comprising presenting on the interface an indication of the lead type that is associated with each of the at least one device connectors.

17. The method of claim 16, further comprising presenting on the interface an indication of the user assignment of the one of the plurality of lead types to the at least one of the device connectors.

18. The method of claim 14, wherein the data obtained from each lead comprises measurements of impedance between each of the electrodes in the group of electrodes and a case of a neurostimulator.

19. The method of claim 14, wherein the data obtained from each lead comprises measurements of impedance between one or more pairs of the electrodes in the group of electrodes.

20. The method of claim 14, wherein the data obtained from each lead comprises measurements of an electric potential that is induced at one or more of the electrodes in the group of electrodes when a current is sourced or sunk from a different one or more of the electrodes.

* * * * *